United States Patent
De Miguel et al.

(10) Patent No.: US 12,115,258 B2
(45) Date of Patent: Oct. 15, 2024

(54) HIGH PERFORMANCE EXCIPIENT COMPRISING CO-PROCESSED MICROCRYSTALLINE CELLULOSE AND SURFACE-REACTED CALCIUM CARBONATE

(71) Applicant: OMYA INTERNATIONAL AG, Oftringen (CH)

(72) Inventors: Laura De Miguel, Zofingen (CH); Stefan Lander, Rupperswil (CH)

(73) Assignee: OMYA INTERNATIONAL AG, Oftringen (CH)

( * ) Notice: Subject to any disclaimer, the term of this patent is extended or adjusted under 35 U.S.C. 154(b) by 618 days.

(21) Appl. No.: 17/275,099

(22) PCT Filed: Sep. 17, 2019

(86) PCT No.: PCT/EP2019/074834
§ 371 (c)(1),
(2) Date: Mar. 10, 2021

(87) PCT Pub. No.: WO2020/058252
PCT Pub. Date: Mar. 26, 2020

(65) Prior Publication Data
US 2022/0047511 A1 Feb. 17, 2022

(30) Foreign Application Priority Data

Sep. 17, 2018 (EP) .................................. 18194903
Jan. 21, 2019 (EP) .................................. 19152843

(51) Int. Cl.
*A61K 9/16* (2006.01)
*A23L 29/00* (2016.01)
*A23P 10/20* (2016.01)

(52) U.S. Cl.
CPC .......... *A61K 9/1611* (2013.01); *A23L 29/015* (2016.08); *A23L 29/035* (2016.08); *A23P 10/20* (2016.08); *A61K 9/1652* (2013.01); *A61K 9/1682* (2013.01)

(58) Field of Classification Search
None
See application file for complete search history.

(56) References Cited

U.S. PATENT DOCUMENTS

| | | | |
|---|---|---|---|
| 4,744,987 A | 5/1988 | Mehra et al. | |
| 5,747,067 A | 5/1998 | Auguello et al. | |
| 6,232,351 B1 | 5/2001 | Ibrahim et al. | |
| 8,632,819 B2 | 1/2014 | Thoorens et al. | |
| 2003/0213937 A1 | 11/2003 | Yaniv | |
| 2011/0151014 A1* | 6/2011 | Thoorens | A61K 9/2054 514/474 |
| 2015/0283082 A1* | 10/2015 | Gerard | A61K 9/2013 424/44 |

FOREIGN PATENT DOCUMENTS

| | | |
|---|---|---|
| CN | 102170867 B | 4/2014 |
| EP | 3269361 A1 | 1/2018 |
| EP | 3275948 * | 1/2018 |
| EP | 3275948 A1 | 1/2018 |
| WO | 2010037753 A1 | 4/2010 |

OTHER PUBLICATIONS

International Search Report and Written Opinion issued in PCT/EP2019/074834 mailed Jan. 3, 2020.
Pharmacy, Shenyang Pharmaceutical College, People's Health Publishing House, 1st Edition, p. 232 with translation. May 31, 1980.

* cited by examiner

*Primary Examiner* — Tigabu Kassa
(74) *Attorney, Agent, or Firm* — Heslin Rothenberg Farley & Mesisi P.C.

(57) ABSTRACT

The present invention refers to a particulate pharmaceutical or nutraceutical excipient, a process for the preparation of the particulate pharmaceutical or nutraceutical excipient, a pharmaceutical or nutraceutical composition comprising the particulate pharmaceutical or nutraceutical excipient as well as a process for manufacturing a pharmaceutical or nutraceutical composition.

20 Claims, 7 Drawing Sheets

HIGH PERFORMANCE EXCIPIENT COMPRISING CO-PROCESSED MICROCRYSTALLINE CELLULOSE AND SURFACE-REACTED CALCIUM CARBONATE

CROSS REFERENCE TO RELATED APPLICATIONS

This application is a U.S. National Phase filing under 35 U.S.C. § 371 of International Application PCT/EP2019/074834, filed Sep. 17, 2019, and published as WO 2020/058252 A1 and corrected publication WO 2020/058252 A9 on Mar. 26, 2020. PCT/EP2019/074834 claims priority from European patent application number 18194903.3, filed Sep. 17, 2018 and European patent application number 19152843.9, filed on Jan. 21, 2019. The entire contents of each of these prior applications are hereby incorporated herein by reference.

The present invention refers to a particulate pharmaceutical or nutraceutical excipient, a process for the preparation of the particulate pharmaceutical or nutraceutical excipient, a pharmaceutical or nutraceutical composition comprising the particulate pharmaceutical or nutraceutical excipient as well as a process for manufacturing a pharmaceutical or nutraceutical composition.

Microcrystalline cellulose is the most commonly used excipient in the pharmaceutical and nutraceutical industry. As a direct compression filler and binder, it features excellent compactability and binding properties. However, the flow properties of this excipient is usually limited and thus further limiting the dilution potential and the formulation of poorly flowable actives. It is thus typically necessary to adapt the properties by adding further materials for improving specific needs.

Excipients for pharmaceutical or nutraceutical applications are well known in the art. For example, U.S. Pat. No. 4,744,987 refers to a composition of matter useful as a pharmaceutical excipient comprising dried particulate agglomerates of coprocessed microcrystalline cellulose and calcium carbonate, the two components being present in a weight ratio of from about 75:25 to 35:65 microcrystalline cellulose:calcium carbonate and intimately associated with each other. The calcium carbonate employed is preferably a precipitated material.

US 2015/0283082 A1 refers to a fast disintegrating dosage form comprising functionalized natural and/or synthetic calcium carbonate, at least one active ingredient and at least one disintegrant, wherein said functionalized natural or synthetic calcium carbonate is a reaction product of natural or synthetic calcium carbonate with carbon dioxide and one or more acids, wherein the carbon dioxide is formed in situ by the acid treatment and/or is supplied from an external source, and wherein the tablet disintegrates in less than or in 3 minutes. The at least one disintegrant may be selected from the group comprising modified cellulose gums, insoluble cross-linked polyvinylpyrrolidones, starch glycolates, micro crystalline cellulose, alkyl-, hydroxyalkyl-, carboxyalkyl-cellulose esters, alginates, microcrystalline cellulose and its polymorphic forms, ion exchange resins, gums, chitin, chitosan, clays, gellan gum, crosslinked polacrillin copolymers, agar, gelatine, dextrines, acrylic acid polymers, carboxymethylcellulose sodium/calcium, hydroxypropyl methyl cellulose phtalate, shellac or mixtures thereof and may be present in the range from about 0.3 wt % to about 10 wt %, based on the weight of functionalized natural or synthetic calcium carbonate.

U.S. Pat. No. 8,632,819 B2 refers to a coprocessed composition useful as a recompactible pharmaceutical excipient comprising particles of calcium carbonate and particles of microcrystalline cellulose, wherein the weight ratio of microcrystalline cellulose:calcium carbonate is from greater than 75:25 up to 85:15. The calcium carbonate is a precipitated calcium carbonate or ground limestone.

U.S. Pat. No. 6,232,351 B1 refers to a direct tabletting agent comprising dried particulates of co-processed: a. plant; b. microcrystalline cellulose; and c. calcium carbonate, wherein the three components are intimately associated with each other. The calcium carbonate is a precipitated material, mined material, or harvested material such as oyster shells.

U.S. Pat. No. 5,747,067 refers to a particulate pharmaceutical tablet excipient compositions comprising co-processed microcrystalline cellulose and particulate USP calcium carbonate, in which the calcium carbonate has an average particle size in the range of 7 to 22 μm and the weight ratio of calcium carbonate to microcrystalline cellulose is in the range of 70:30 to 90:10. The calcium carbonate is ground limestone or precipitated calcium carbonate.

However, there is a constant need for excipients suitable for pharmaceutical and nutraceutical applications providing high flowability properties and high bulk density. In addition thereto, it is desired to provide excipients having a fast disintegration times, less dependency on hardness as well as less lubricant sensitivity and improved drug distribution throughout the final composition. Furthermore, it is desired that the excipient has higher compactability properties than microcrystalline cellulose and thus allowing the tableting of poorly compactable actives and reducing or eliminating the use of other excipients.

Accordingly, an objective of the present invention may be seen in the provision of an excipient suitable for pharmaceutical and nutraceutical applications. Another objective of the present application is the provision of an excipient providing high flowability properties and high bulk density as well as fastened disintegration times and less dependency on hardness. A further objective of the present application is the provision of an excipient providing less lubricant sensitivity and improved drug distribution throughout the final composition. A still further objective of the present application is the provision of an excipient having higher compactability properties than microcrystalline cellulose and thus allowing the tableting of poorly compactable actives and reducing or eliminating the use of other excipients.

The foregoing objects and other objects are solved by the subject-matter as defined herein in the independent claims. Advantageous embodiments of the present invention are defined herein and also in the corresponding sub-claims.

According to one aspect of the present invention, a particulate pharmaceutical or nutraceutical excipient is provided. The excipient comprising a) microcrystalline cellulose, and b) surface-reacted calcium carbonate, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source, wherein the weight ratio of the microcrystalline cellulose to the surface-reacted calcium carbonate is from 99.9:0.1 to 50:50.

According to one embodiment, the surface-reacted calcium carbonate has i) a volume median particle size $d_{50}$ from 0.5 to 50 μm, more preferably from 1 to 40 μm, even more preferably from 1.2 to 30 μm, and most preferably from 1.5 to 15 µm, and/or ii) a BET specific surface area of from 5 to 200 m$^2$/g, preferably from 15 to 150 m$^2$/g, more preferably from 40 to 100 m$^2$/g, measured using nitrogen and the BET method according to ISO 9277:2010, and/or iii) an intra-particle intruded specific pore volume in the range from 0.1 to 2.3 cm$^3$/g, more preferably from 0.2 to 2.0 cm$^3$/g, especially preferably from 0.4 to 1.8 cm$^3$/g and most preferably from 0.6 to 1.6 cm$^3$/g, calculated from mercury porosimetry measurement.

According to another embodiment, i) the natural ground calcium carbonate is selected from the group consisting of marble, chalk, limestone, and mixtures thereof, or ii) the precipitated calcium carbonate is selected from the group consisting of precipitated calcium carbonates having an aragonitic, vateritic or calcitic crystal form, and mixtures thereof.

According to yet another embodiment, the at least one $H_3O^+$ ion donor is selected from the group consisting of hydrochloric acid, sulphuric acid, sulphurous acid, phosphoric acid, citric acid, oxalic acid, an acidic salt, acetic acid, formic acid, and mixtures thereof, preferably the at least one $H_3O^+$ ion donor is selected from the group consisting of hydrochloric acid, sulphuric acid, sulphurous acid, phosphoric acid, oxalic acid, $H_2PO_4-$, being at least partially neutralised by a cation selected from Li$^+$, Na$^+$ and/or K$^+$, $HPO_4^{2-}$, being at least partially neutralised by a cation selected from Li$^+$, Na$^+$, K$^+$, Mg$^{2+}$, and/or Ca$^{2+}$, and mixtures thereof, more preferably the at least one $H_3O^+$ ion donor is selected from the group consisting of hydrochloric acid, sulphuric acid, sulphurous acid, phosphoric acid, oxalic acid, or mixtures thereof, and most preferably, the at least one $H_3O^+$ ion donor is phosphoric acid.

According to one embodiment, the microcrystalline cellulose has a i) a loose bulk density from 0.20 to 0.52 g/ml, more preferably from 0.26 to 0.36 g/ml, and/or ii) a weight median particle size d$_{50}$ from 10 to 1000 µm, preferably from 15 to 500 µm, most preferably from 20 to 200 µm.

According to another embodiment, the weight ratio of the microcrystalline cellulose to the surface-reacted calcium carbonate is from 99.9:0.1 to 75:25, preferably from 99:1 to 80:20, and most preferably from 98:2 to 90:10.

According to yet another embodiment, the excipient comprises co-processed microcrystalline cellulose and surface-reacted calcium carbonate in that the surface-reacted calcium carbonate is in intimate association with the microcrystalline cellulose.

According to one embodiment, the excipient has a loose bulk density from 0.25 to 0.90 g/ml, more preferably from 0.25 to 0.65 g/ml.

According to another aspect, a process for the preparation of the particulate pharmaceutical or nutraceutical excipient as defined herein is provided. The process comprises the steps of:
  a) mixing microcrystalline cellulose and surface-reacted calcium carbonate, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source, in a weight ratio of the microcrystalline cellulose to the surface-reacted calcium carbonate from 99.9:0.1 to 50:50, and
  b) co-processing the mixture obtained in step a) obtaining thereby the particulate pharmaceutical or nutraceutical excipient.

According to one embodiment of the process, co-processing step b) is performed by dry- or wet-processing, preferably high-shear mixing, spray drying, milling or mixtures thereof.

According to another embodiment of the process, mixing step a) is performed in an aqueous medium such as to form an aqueous slurry comprising the microcrystalline cellulose and the surface-reacted calcium carbonate.

According to a further aspect, a pharmaceutical or nutraceutical composition comprising the particulate pharmaceutical or nutraceutical excipient as defined herein and optionally at least one active ingredient, preferably the at least one active ingredient is selected from the group comprising pharmaceutically or nutraceutically active ingredients, inactive pharmaceutical or nutraceutical precursors, biologically active ingredients, inactive biological precursors and mixtures thereof if provided.

According to one embodiment, the pharmaceutical or nutraceutical composition further comprises at least one adjuvant selected from the group comprising natural or synthetic scenting agents, natural or synthetic flavoring agents, natural or synthetic coloring agents, natural or synthetic sweeteners, lubricants, disintegrants, glidants, and mixtures thereof.

According to a still further aspect, a process for manufacturing a pharmaceutical or nutraceutical composition as defined herein is provided. The process comprises the steps of:
  a) providing a particulate pharmaceutical or nutraceutical excipient as defined herein,
  b) subjecting the particulate pharmaceutical or nutraceutical excipient to dry granulation, wet granulation, melt granulation or direct compression, preferably direct compression, obtaining thereby the composition.

According to one embodiment, the process further comprises a step c) of contacting the particulate pharmaceutical or nutraceutical excipient before step b) or the composition obtained in step b) with at least one active ingredient, preferably the at least one active ingredient is selected from the group comprising pharmaceutically or nutraceutically active ingredients, inactive pharmaceutical or nutraceutical precursors, biologically active ingredients, inactive biological precursors and mixtures thereof, and/or at least one adjuvant selected from the group comprising natural or synthetic scenting agents, natural or synthetic flavoring agents, natural or synthetic coloring agents, natural or synthetic sweeteners, lubricants, disintegrants, glidants, and mixtures thereof.

It should be understood that for the purposes of the present invention, the following terms have the following meanings:

The term "excipient" refers to a non active material/ingredient that is formulated alongside a pharmaceutical or nutraceutical active ingredient. The excipients are intentionally added in the composition in order to enable active ingredient to be applied to the user in the correct form and act as the vehicle for the active ingredients. It is appreciated that the excipient has no medicinal properties.

The term "pharmaceutical" excipient refers to an excipient that is suitable for formulating pharmaceutically active ingredients into pharmaceutical compositions, such as pharmaceutical dosage forms.

The term "nutraceutical" excipient refers to an excipient that is suitable for formulating nutraceutically active ingredients into neutraceutical compositions, such as neutraceutical dosage forms.

"Natural ground calcium carbonate" (GCC) in the meaning of the present invention is a calcium carbonate obtained from natural sources, such as limestone, marble, or chalk, and processed through a wet and/or dry treatment such as grinding, screening and/or fractionating, for example, by a cyclone or classifier.

"Precipitated calcium carbonate" (PCC) in the meaning of the present invention is a synthesised material, obtained by precipitation following reaction of carbon dioxide and lime in an aqueous, semi-dry or humid environment or by precipitation of a calcium and carbonate ion source in water. PCC may be in the vateritic, calcitic or aragonitic crystal form. PCCs are described, for example, in EP 2 447 213 A1, EP 2 524 898 A1, EP 2 371 766 A1, EP 1 712 597 A1, EP 1 712 523 A1, or WO 2013/142473 A1.

The term "surface-reacted" in the meaning of the present application shall be used to indicate that a material has been subjected to a process comprising partial dissolution of said material upon treatment with an $H_3O^+$ ion donor (e.g., by use of water-soluble free acids and/or acidic salts) in aqueous environment followed by a crystallization process which may occur in the absence or presence of further crystallization additives.

An "$H_3O^+$ ion donor" in the context of the present invention is a Brønsted acid and/or an acid salt, i.e. a salt containing an acidic hydrogen.

The term "acid" as used herein refers to an acid in the meaning of the definition by Brønsted and Lowry (e.g., $H_2SO_4$. $HSO_4-$).

Where the term "comprising" is used in the present description and claims, it does not exclude other non-specified elements of major or minor functional importance. For the purposes of the present invention, the term "consisting of" is considered to be a preferred embodiment of the term "comprising of". If hereinafter a group is defined to comprise at least a certain number of embodiments, this is also to be understood to disclose a group, which preferably consists only of these embodiments.

Whenever the terms "including" or "having" are used, these terms are meant to be equivalent to "comprising" as defined above.

Where an indefinite or definite article is used when referring to a singular noun, e.g. "a", "an" or "the", this includes a plural of that noun unless something else is specifically stated.

Terms like "obtainable" or "definable" and "obtained" or "defined" are used interchangeably. This e.g. means that, unless the context clearly dictates otherwise, the term "obtained" does not mean to indicate that e.g. an embodiment must be obtained by e.g. the sequence of steps following the term "obtained" even though such a limited understanding is always included by the terms "obtained" or "defined" as a preferred embodiment.

In the following details and preferred embodiments of the inventive excipient will be set out in more detail. It is to be understood that these technical details and embodiments also apply to all of the inventive products and processes.

Particulate Pharmaceutical or Nutraceutical Excipient

The particulate pharmaceutical or nutraceutical excipient comprises a) microcrystalline cellulose, and b) surface-reacted calcium carbonate, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source, wherein the weight ratio of the microcrystalline cellulose to the surface-reacted calcium carbonate is from 99.9:0.1 to 50:50.

Thus, it is one requirement of the present invention that the particulate pharmaceutical or nutraceutical excipient comprises microcrystalline cellulose.

The microcrystalline cellulose is preferably prepared by partially depolymerizing cellulose obtained as a pulp from fibrous plant material with dilute mineral acid solutions. Following hydrolysis, the hydrocellulose thereby obtained is purified via filtration and the aqueous slurry may be spray dried to obtain the dried microcrystalline cellulose. Alternatively, cellulose may be subjected to a hydrolytic treatment with hydrochloric acid at boiling temperatures such that amorphous parts are removed and aggregates of crystalline cellulose are formed. The aggregates may be collected by filtration, washed with water and aqueous ammonia and disintegrated into small fragments by vigorous mechanical means such as a blender.

The source and the nature of the microcrystalline cellulose are not considered critical. Thus, the microcrystalline cellulose can be any microcrystalline cellulose known as being suitable for pharmaceutical or nutraceutical applications.

For example, the microcrystalline cellulose can be a wet cake from a conventional microcrystalline cellulose manufacturing process, i.e. a material which has not been dried. The microcrystalline cellulose may be also a conventional microcrystalline cellulose that has been dried.

The weight median particle size $d_{50}$ of the microcrystalline cellulose is preferably from 10 to 1000 μm, more preferably from 15 to 500 μm and most preferably from 20 to 200 μm.

Additionally or alternatively, the microcrystalline cellulose has a loose bulk density from 0.20 to 0.52 g/ml and more preferably from 0.26 to 0.36 g/ml.

For example, the microcrystalline cellulose has a loose bulk density from 0.20 to 0.52 g/ml and more preferably from 0.26 to 0.36 g/ml or a weight median particle size $d_{50}$ from 10 to 1000 μm, preferably from 15 to 500 μm and most preferably from 20 to 200 μm.

Alternatively, the microcrystalline cellulose has a loose bulk density from 0.20 to 0.52 g/ml and more preferably from 0.26 to 0.36 g/ml and a weight median particle size $d_{50}$ from 10 to 1000 μm, preferably from 15 to 500 μm and most preferably from 20 to 200 μm.

A further requirement of the present invention is that the excipient comprises surface-reacted calcium carbonate.

It is appreciated that the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source.

In a preferred embodiment, the surface-reacted calcium carbonate is obtained by a process comprising the steps of: (a) providing a suspension of natural or precipitated calcium carbonate, (b) adding at least one acid having a $pK_a$ value of 0 or less at 20° C. or having a $pK_a$ value from 0 to 2.5 at 20° C. to the suspension of step a), and (c) treating the suspension of step (a) with carbon dioxide before, during or after step (b). According to another embodiment the surface-reacted calcium carbonate is obtained by a process comprising the steps of: (A) providing a natural or precipitated calcium carbonate, (B) providing at least one water-soluble acid, (C) providing gaseous $CO_2$, (D) contacting said natural or precipitated calcium carbonate of step (A) with the at least one acid of step (B) and with the $CO_2$ of step (C), characterised in that: (i) the at least one acid of step B) has a $pK_a$ of greater than 2.5 and less than or equal to 7 at 20° C., associated with the ionisation of its first available hydrogen, and a corresponding anion is formed on loss of this first available hydrogen capable of forming a water-soluble calcium salt, and (ii) following contacting the at least one acid with natural or precipitated calcium carbonate, at least one water-soluble salt, which in the case of a hydrogen-containing salt has a $pK_a$ of greater than 7 at 20° C., associated with the ionisation of the first available hydrogen, and the salt anion of which is capable of forming water-insoluble calcium salts, is additionally provided.

"Natural ground calcium carbonate" (GCC) preferably is selected from calcium carbonate containing minerals selected from the group comprising marble, chalk, limestone and mixtures thereof. Natural ground calcium carbonate may comprise further naturally occurring components such as magnesium carbonate, alumino silicate etc.

In general, the grinding of natural ground calcium carbonate may be a dry or wet grinding step and may be carried out with any conventional grinding device, for example, under conditions such that comminution predominantly results from impacts with a secondary body, i.e. in one or more of: a ball mill, a rod mill, a vibrating mill, a roll crusher, a centrifugal impact mill, a vertical bead mill, an attrition mill, a pin mill, a hammer mill, a pulveriser, a shredder, a de-clumper, a knife cutter, or other such equipment known to the skilled man. In case the calcium carbonate containing mineral material comprises a wet ground calcium carbonate containing mineral material, the grinding step may be performed under conditions such that autogenous grinding takes place and/or by horizontal ball milling, and/or other such processes known to the skilled man. The wet processed ground calcium carbonate containing mineral material thus obtained may be washed and dewatered by well-known processes, e.g. by flocculation, filtration or forced evaporation prior to drying. The subsequent step of drying (if necessary) may be carried out in a single step such as spray drying, or in at least two steps. It is also common that such a mineral material undergoes a beneficiation step (such as a flotation, bleaching or magnetic separation step) to remove impurities.

"Precipitated calcium carbonate" (PCC) in the meaning of the present invention is a synthesized material, generally obtained by precipitation following reaction of carbon dioxide and calcium hydroxide in an aqueous environment or by precipitation of calcium and carbonate ions, for example $CaCl_2$) and $Na_2CO_3$, out of solution. Further possible ways of producing PCC are the lime soda process, or the Solvay process in which PCC is a by-product of ammonia production. Precipitated calcium carbonate exists in three primary crystalline forms: calcite, aragonite and vaterite, and there are many different polymorphs (crystal habits) for each of these crystalline forms. Calcite has a trigonal structure with typical crystal habits such as scalenohedral (S-PCC), rhombohedral (R-PCC), hexagonal prismatic, pinacoidal, colloidal (C-PCC), cubic, and prismatic (P-PCC). Aragonite is an orthorhombic structure with typical crystal habits of twinned hexagonal prismatic crystals, as well as a diverse assortment of thin elongated prismatic, curved bladed, steep pyramidal, chisel shaped crystals, branching tree, and coral or worm-like form. Vaterite belongs to the hexagonal crystal system. The obtained PCC slurry can be mechanically dewatered and dried.

According to one embodiment of the present invention, the precipitated calcium carbonate is precipitated calcium carbonate, preferably comprising aragonitic, vateritic or calcitic mineralogical crystal forms or mixtures thereof.

Precipitated calcium carbonate may be ground prior to the treatment with carbon dioxide and at least one $H_3O^+$ ion donor by the same means as used for grinding natural calcium carbonate as described above.

According to one embodiment of the present invention, the natural ground calcium carbonate or precipitated calcium carbonate is in form of particles having a weight median particle size $d_{50}$ of 0.05 to 10.0 μm, preferably 0.2 to 5.0 μm, and most preferably 0.4 to 3.0 μm. According to a further embodiment of the present invention, the natural ground calcium carbonate or precipitated calcium carbonate is in form of particles having a weight top cut particle size $d_{98}$ of 0.15 to 30 μm, preferably 0.6 to 15 μm, more preferably 1.2 to 10 μm, most preferably 1.5 to 4 μm, especially 1.6 μm.

The natural ground calcium carbonate and/or precipitated calcium carbonate may be used dry or suspended in water. Preferably, a corresponding slurry has a content of natural ground calcium carbonate or precipitated calcium carbonate within the range of 1 wt.-% to 90 wt.-%, more preferably 3 wt.-% to 60 wt.-%, even more preferably 5 wt.-% to 40 wt.-%, and most preferably 10 wt.-% to 25 wt.-% based on the weight of the slurry.

The one or more $H_3O^+$ ion donor used for the preparation of surface-reacted calcium carbonate may be any strong acid, medium-strong acid, or weak acid, or mixtures thereof, generating $H_3O^+$ ions under the preparation conditions. According to the present invention, the at least one $H_3O^+$ ion donor can also be an acid salt, generating $H_3O^+$ ions under the preparation conditions.

According to one embodiment, the at least one $H_3O^+$ ion donor is a strong acid having a $pK_a$ of 0 or less at 20° C.

According to another embodiment, the at least one $H_3O^+$ ion donor is a medium-strong acid having a $pK_a$ value from 0 to 2.5 at 20° C. If the $pK_a$ at 20° C. is 0 or less, the acid is preferably selected from sulphuric acid, hydrochloric acid, or mixtures thereof. If the $pK_a$ at 20° ° C. is from 0 to 2.5, the $H_3O^+$ ion donor is preferably selected from $H_2SO_3$, $H_3PO_4$, oxalic acid, or mixtures thereof. The at least one $H_3O^+$ ion donor can also be an acid salt, for example, $HSO_4$ or $H_2PO_4$, being at least partially neutralized by a corresponding cation such as $Li^+$, $Na^+$ or $K^+$, or $HPO_4^{2-}$, being at least partially neutralised by a corresponding cation such as $Li^+$, $Na^+$. $K^+$, $Mg^{2+}$ or $Ca^{2+}$. The at least one $H_3O^+$ ion donor can also be a mixture of one or more acids and one or more acid salts.

According to still another embodiment, the at least one $H_3O^+$ ion donor is a weak acid having a $pK_a$ value of greater than 2.5 and less than or equal to 7, when measured at 20° C., associated with the ionisation of the first available hydrogen, and having a corresponding anion, which is capable of forming water-soluble calcium salts. Subsequently, at least one water-soluble salt, which in the case of a hydrogen-containing salt has a $pK_a$ of greater than 7, when measured at 20° C., associated with the ionisation of the first available hydrogen, and the salt anion of which is capable of forming water-insoluble calcium salts, is additionally provided. According to the preferred embodiment, the weak acid has a $pK_a$ value from greater than 2.5 to 5 at 20° C., and more preferably the weak acid is selected from the group consisting of acetic acid, formic acid, propanoic acid, and mixtures thereof. Exemplary cations of said water-soluble salt are selected from the group consisting of potassium, sodium, lithium and mixtures thereof. In a more preferred embodiment, said cation is sodium or potassium. Exemplary anions of said water-soluble salt are selected from the group consisting of phosphate, dihydrogen phosphate, monohydrogen phosphate, oxalate, silicate, mixtures thereof and hydrates thereof. In a more preferred embodiment, said anion is selected from the group consisting of phosphate, dihydrogen phosphate, monohydrogen phosphate, mixtures thereof and hydrates thereof. In a most preferred embodiment, said anion is selected from the group consisting of dihydrogen phosphate, monohydrogen phosphate, mixtures thereof and hydrates thereof. Water-soluble salt addition may be performed dropwise or in one step. In the case of drop wise addition, this addition preferably takes place within a time period of 10 minutes. It is more preferred to add said salt in one step.

According to one embodiment of the present invention, the at least one $H_3O^+$ ion donor is selected from the group consisting of hydrochloric acid, sulphuric acid, sulphurous acid, phosphoric acid, citric acid, oxalic acid, acetic acid, formic acid, and mixtures thereof. Preferably the at least one $H_3O^+$ ion donor is selected from the group consisting of hydrochloric acid, sulphuric acid, sulphurous acid, phosphoric acid, oxalic acid, $H_2PO_4^-$, being at least partially neutralised by a corresponding cation such as $Li^+$, $Na^+$ or $K^+$, $HPO_4^{2-}$, being at least partially neutralised by a corresponding cation such as $Li^+$, $Na^+$. $K^+$, $Mg^{2+}$, or $Ca^{2+}$ and mixtures thereof, more preferably the at least one acid is selected from the group consisting of hydrochloric acid, sulphuric acid, sulphurous acid, phosphoric acid, oxalic acid, or mixtures thereof, and most preferably, the at least one $H_3O^+$ ion donor is phosphoric acid.

The one or more $H_3O^+$ ion donor can be added to the suspension as a concentrated solution or a more diluted solution. Preferably, the molar ratio of the $H_3O^+$ ion donor to the natural or precipitated calcium carbonate is from 0.01 to 4, more preferably from 0.02 to 2, even more preferably 0.05 to 1 and most preferably 0.1 to 0.58.

As an alternative, it is also possible to add the $H_3O^+$ ion donor to the water before the natural or precipitated calcium carbonate is suspended.

In a next step, the natural ground calcium carbonate or precipitated calcium carbonate is treated with carbon dioxide. If a strong acid such as sulphuric acid or hydrochloric acid is used for the $H_3O^+$ ion donor treatment of the natural ground calcium carbonate or precipitated calcium carbonate, the carbon dioxide is automatically formed. Alternatively or additionally, the carbon dioxide can be supplied from an external source.

$H_3O^+$ ion donor treatment and treatment with carbon dioxide can be carried out simultaneously which is the case when a strong or medium-strong acid is used. It is also possible to carry out $H_3O^+$ ion donor treatment first, e.g. with a medium strong acid having a $pK_a$ in the range of 0 to 2.5 at 20° C., wherein carbon dioxide is formed in situ, and thus, the carbon dioxide treatment will automatically be carried out simultaneously with the $H_3O^+$ ion donor treatment, followed by the additional treatment with carbon dioxide supplied from an external source.

Preferably, the concentration of gaseous carbon dioxide in the suspension is, in terms of volume, such that the ratio (volume of suspension):(volume of gaseous $CO_2$) is from 1:0.05 to 1:20, even more preferably 1:0.05 to 1:5.

In a preferred embodiment, the $H_3O^+$ ion donor treatment step and/or the carbon dioxide treatment step are repeated at least once, more preferably several times. According to one embodiment, the at least one $H_3O^+$ ion donor is added over a time period of at least about 5 min, typically from about 5 to about 30 min. Alternatively, the at least one $H_3O^+$ ion donor is added over a time period of about 30 min, preferably about 45 min, and sometimes about 1 h or more.

Subsequent to the $H_3O^+$ ion donor treatment and carbon dioxide treatment, the pH of the aqueous suspension, measured at 20° C., naturally reaches a value of greater than 6.0, preferably greater than 6.5, more preferably greater than 7.0, even more preferably greater than 7.5, thereby preparing the surface-reacted natural or precipitated calcium carbonate as an aqueous suspension having a pH of greater than 6.0, preferably greater than 6.5, more preferably greater than 7.0, even more preferably greater than 7.5.

It is appreciated that the $H_3O^+$ ion donor treatment and treatment with carbon dioxide can be carried over a wide temperature range. Preferably, the $H_3O^+$ ion donor treatment and treatment with carbon dioxide can be carried out at room temperature or elevated temperature. For example, if the $H_3O^+$ ion donor treatment and treatment with carbon dioxide is carried out at elevated temperature, the treatment is preferably in a range from 30 to 90° C., more preferably from 40 to 80° C. and most preferably from 50 to 80° C., such as from 60 to 80° C.

Further details about the preparation of the surface-reacted natural calcium carbonate are disclosed in WO 00/39222 A1, WO 2004/083316 A1, WO 2005/121257 A2, WO 2009/074492 A1, EP 2 264 108 A1, EP 2 264 109 A1 and US 2004/0020410 A1, the content of these references herewith being included in the present application.

Similarly, surface-reacted precipitated calcium carbonate is obtained. As can be taken in detail from WO 2009/074492 A1, surface-reacted precipitated calcium carbonate is obtained by contacting precipitated calcium carbonate with $H_3O^+$ ions and with anions being solubilized in an aqueous medium and being capable of forming water-insoluble calcium salts, in an aqueous medium to form a slurry of surface-reacted precipitated calcium carbonate, wherein said surface-reacted precipitated calcium carbonate comprises an insoluble, at least partially crystalline calcium salt of said anion formed on the surface of at least part of the precipitated calcium carbonate.

Said solubilized calcium ions correspond to an excess of solubilized calcium ions relative to the solubilized calcium ions naturally generated on dissolution of precipitated calcium carbonate by $H_3O^+$ ions, where said $H_3O^+$ ions are provided solely in the form of a counterion to the anion, i.e. via the addition of the anion in the form of an acid or non-calcium acid salt, and in absence of any further calcium ion or calcium ion generating source.

Said excess solubilized calcium ions are preferably provided by the addition of a soluble neutral or acid calcium salt, or by the addition of an acid or a neutral or acid non-calcium salt which generates a soluble neutral or acid calcium salt in situ.

Said $H_3O^+$ ions may be provided by the addition of an acid or an acid salt of said anion, or the addition of an acid or an acid salt which simultaneously serves to provide all or part of said excess solubilized calcium ions.

In a further preferred embodiment of the preparation of the surface-reacted natural ground calcium carbonate or precipitated calcium carbonate, the natural ground calcium carbonate or precipitated calcium carbonate is reacted with the acid and/or the carbon dioxide in the presence of at least one compound selected from the group consisting of silicate, silica, aluminium hydroxide, earth alkali aluminate such as sodium or potassium aluminate, magnesium oxide, or mixtures thereof. Preferably, the at least one silicate is selected from an aluminium silicate, a calcium silicate, or an earth alkali metal silicate. These components can be added to an aqueous suspension comprising the natural ground calcium carbonate or precipitated calcium carbonate before adding the acid and/or carbon dioxide.

Alternatively, the silicate and/or silica and/or aluminium hydroxide and/or earth alkali aluminate and/or magnesium oxide component(s) can be added to the aqueous suspension of natural or precipitated calcium carbonate while the reaction of natural or precipitated calcium carbonate with an acid and carbon dioxide has already started. Further details about the preparation of the surface-reacted natural or precipitated calcium carbonate in the presence of at least one silicate and/or silica and/or aluminium hydroxide and/or earth alkali aluminate component(s) are disclosed in WO 2004/083316 A1, the content of this reference herewith being included in the present application.

The surface-reacted calcium carbonate can be kept in suspension, optionally further stabilised by a dispersant. Conventional dispersants known to the skilled person can be used. A preferred dispersant is comprised of polyacrylic acids and/or carboxymethylcelluloses.

Alternatively, the aqueous suspension described above can be dried, thereby obtaining the solid (i.e. dry or containing as little water that it is not in a fluid form) surface-reacted natural ground calcium carbonate or precipitated calcium carbonate in the form of granules or a powder.

The surface-reacted calcium carbonate may have different particle shapes, such as e.g. the shape of roses, golf balls and/or brains.

According to one embodiment, the surface-reacted calcium carbonate has a specific surface area of from 5 $m^2/g$ to 200 $m^2/g$, preferably from 15 $m^2/g$ to 150 $m^2/g$, and most preferably from 40 $m^2/g$ to 100 $m^2/g$, measured using nitrogen and the BET method. The BET specific surface area in the meaning of the present invention is defined as the surface area of the particles divided by the mass of the particles. As used therein the specific surface area is measured by adsorption using the BET isotherm (ISO 9277: 2010) and is specified in $m^2/g$.

Additionally or alternatively, the surface-reacted calcium carbonate has a volume median particle size $d_{50}$ from 0.5 to 50 µm, preferably from 1 to 40 µm, more preferably from 1.2 to 30 µm, and most preferably from 1.5 to 15 µm.

It may furthermore be preferred that the surface-reacted calcium carbonate particles have a volume top cut particle size $d_{98}$ of from 2 to 150 µm, preferably from 4 to 100 µm, more preferably 6 to 80 µm, even more preferably from 8 to 60 µm, and most preferably from 8 to 30 µm.

Throughout the present application, the value $d_x$ represents the diameter relative to which x % of the particles have diameters less than $d_x$. This means that the d98 value is the particle size at which 98% of all particles are smaller. The d98 value is also designated as "top cut". The $d_x$ values may be given in volume or weight percent. The $d_{50}$(wt) value is thus the weight median particle size, i.e. 50 wt.-% of all grains are smaller than this particle size, and the $d_{50}$ (vol) value is the volume median particle size, i.e. 50 vol. % of all grains are smaller than this particle size.

The "particle size" of surface-reacted calcium carbonate herein is described as volume-based particle size distribution. Volume median grain diameter $d_{50}$ was evaluated using a Malvern Mastersizer 2000 Laser Diffraction System. The $d_{50}$ or $d_{98}$ value, measured using a Malvern Mastersizer 2000 Laser Diffraction System, indicates a diameter value such that 50% or 98% by volume, respectively, of the particles have a diameter of less than this value. The raw data obtained by the measurement are analysed using the Mie theory, with a particle refractive index of 1.57 and an absorption index of 0.005.

Throughout the present invention, the weight median grain diameter is determined by the sedimentation method, which is an analysis of sedimentation behaviour in a gravimetric field. The measurement is made with a Sedigraph™ 5120, Micromeritics Instrument Corporation. The method and the instrument are known to the skilled person and are commonly used to determine grain size of fillers and pigments. The measurement is carried out in an aqueous solution of 0.1 wt.-% $Na_4P_2O_7$. The samples were dispersed using a high speed stirrer and sonicated.

The processes and instruments are known to the skilled person and are commonly used to determine grain size of fillers and pigments.

The excipient is mainly used as filler and/or binder in final compositions. It is also capable of associating and transporting an active ingredient. The association preferably is an adsorption, i.e. a loading, onto the surface of and/or inside the excipient. It is appreciated that a loading of the excipient with the at least one active ingredient can be achieved via different methods well known to the skilled person.

Preferably, the surface-reacted calcium carbonate has an intra-particle porosity within the range of from 5 vol.-% to 50 vol.-%, preferably of from 20 vol.-% to 50 vol.-%, especially of from 30 vol.-% to 50 vol.-% calculated from a mercury porosimetry measurement.

Thus, the intra-particle porosity determined as the pore volume per unit particle volume is preferably within the range of from 20 vol.-% to 99 vol.-%, more preferably from 30 vol.-% to 80 vol.-%, even more preferably from 40 vol.-% to 70 vol.-% and most preferably from 50 vol.-% to 65 vol.-%, calculated from mercury porosimetry measurement.

Preferably, the surface-reacted calcium carbonate has an intra-particle intruded specific pore volume in the range from 0.1 to 2.3 $cm^3/g$, more preferably from 0.2 to 2.0 $cm^3/g$, especially preferably from 0.4 to 1.8 $cm^3/g$ and most preferably from 0.6 to 1.6 $cm^3/g$, calculated from mercury porosimetry measurement.

The intra-particle pore size of the surface-reacted calcium carbonate preferably is in a range of from 0.004 to 1.6 µm, more preferably in a range of between 0.005 to 1.3 µm, especially preferably from 0.006 to 1.15 µm and most preferably of 0.007 to 1.0 µm, e.g. 0.004 to 0.16 µm determined by mercury porosimetry measurement.

According to an exemplary embodiment, the surface-reacted calcium carbonate has a volume median particle size $d_{50}$ from 0.5 to 50 µm, more preferably from 1 to 40 µm, even more preferably from 1.2 to 30 µm, and most preferably from 1.5 to 15 µm, and/or a BET specific surface area of from 5 to 200 $m^2/g$, preferably from 15 to 150 $m^2/g$, more preferably from 40 to 100 $m^2/g$, measured using nitrogen and the BET method according to ISO 9277:2010; and/or an intra-particle intruded specific pore volume in the range from 0.1 to 2.3 $cm^3/g$, more preferably from 0.2 to 2.0 $cm^3/g$, especially preferably from 0.4 to 1.8 $cm^3/g$ and most preferably from 0.6 to 1.6 $cm^3/g$, calculated from mercury porosimetry measurement.

For example, the surface-reacted calcium carbonate has a volume median particle size $d_{50}$ from 0.5 to 50 µm, more preferably from 1 to 40 µm, even more preferably from 1.2 to 30 µm, and most preferably from 1.5 to 15 µm, and a BET specific surface area of from 5 to 200 $m^2/g$, preferably from 15 to 150 $m^2/g$, more preferably from 40 to 100 $m^2/g$, measured using nitrogen and the BET method according to ISO 9277:2010; and an intra-particle intruded specific pore volume in the range from 0.1 to 2.3 cm$^3$/g, more preferably from 0.2 to 2.0 cm$^3$/g, especially preferably from 0.4 to 1.8 cm$^3$/g and most preferably from 0.6 to 1.6 cm$^3$/g, calculated from mercury porosimetry measurement.

According to one embodiment of the present invention, the surface-reacted calcium carbonate comprises an water-insoluble, at least partially crystalline calcium salt of an anion of the at least one acid, which is formed on the surface of the natural ground calcium carbonate or precipitated calcium carbonate. According to one embodiment, the water-insoluble, at least partially crystalline salt of an anion of the at least one acid covers the surface of the natural ground calcium carbonate or precipitated calcium carbonate at least partially, preferably completely. Depending on the employed at least one acid, the anion may be sulphate, sulphite, phosphate, citrate, oxalate, acetate, formiate and/or chloride.

For example, the use of phosphoric acid, $H_2PO_4$ or $HPO_4^2$ as the $H_3O^+$ ion donor may lead to the formation of hydroxylapatite. Therefore, in a preferred embodiment, the at least one water-insoluble calcium salt is hydroxylapatite.

According to one embodiment, the at least one water-insoluble calcium salt is hydroxylapatite, wherein the surface-reacted calcium carbonate provides a ratio of hydroxylapatite to calcite, aragonite and/or vaterite, preferably to calcite, in the range of from 1:99 to 99:1 by weight. Preferably, the surface-reacted calcium carbonate may provide a ratio of hydroxylapatite to calcite, aragonite and/or vaterite, preferably to calcite, in the range of from 1:9 to 9:1, preferably 1:7 to 8:1, more preferably 1:5 to 7:1 and most preferably 1:4 to 7:1 by weight.

In a similar manner, the use of other $H_3O^+$ ion donors may lead to the formation of corresponding water-insoluble calcium salts other than calcium carbonate on at least part of the surface of the surface-reacted calcium carbonate. In one embodiment, the at least one water-insoluble calcium salt is thus selected from the group consisting of octacalcium phosphate, hydroxylapatite, chlorapatite, fluorapatite, carbonate apatite and mixtures thereof, wherein the surface-reacted calcium carbonate shows a ratio of the at least one water-insoluble calcium salt to calcite, aragonite and/or vaterite, preferably to calcite, in the range of from 1:99 to 99:1, preferably from 1:9 to 9:1, more preferably from 1:7 to 8:1, even more preferably from 1:5 to 7:1 and most preferably from 1:4 to 7:1 by weight.

For achieving the advantages of the present invention, it is required that the weight ratio of the microcrystalline cellulose (MCC) to the surface-reacted calcium carbonate (SRCC) is from 99.9:0.1 to 50:50. Preferably, the weight ratio of the microcrystalline cellulose (MCC) to the surface-reacted calcium carbonate (SRCC) is from 99.9:0.1 to 75:25, preferably from 99:1 to 80:20, and most preferably from 98:2 to 90:10.

It is appreciated that the microcrystalline cellulose to the surface-reacted calcium carbonate of the present excipient are in intimate association with each other. Thus, the microcrystalline cellulose and surface-reacted calcium carbonate are preferably co-processed.

That is to say, the excipient comprises co-processed microcrystalline cellulose and surface-reacted calcium carbonate in that the surface-reacted calcium carbonate is in intimate association with the microcrystalline cellulose. Preferably, the excipient is obtained by a process comprising the steps of:
  a) mixing microcrystalline cellulose and surface-reacted calcium carbonate, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source, in a weight ratio of the microcrystalline cellulose to the surface-reacted calcium carbonate from 99.9:0.1 to 50:50, and
  b) co-processing the mixture obtained in step a) obtaining thereby the particulate pharmaceutical or nutraceutical excipient.

Preferably, the co-processing in step b) is performed by dry- or wet-processing, preferably high-shear mixing, spray drying, milling or mixtures thereof.

The term "particulate" in the meaning of the present application refers to an excipient composed of a plurality of particles. Said plurality of particles may be defined, for example, by its particle size distribution. The expression "particulate" may comprise granules, powders, grains, tablets, or crumbles.

It is preferred that the excipient has a loose bulk density from 0.25 to 0.90 g/ml, more preferably from 0.25 to 0.65 g/ml.

According to another aspect, the present invention refers to a process for the preparation of the particulate pharmaceutical or nutraceutical excipient. The process comprising the steps of:
  a) mixing microcrystalline cellulose and surface-reacted calcium carbonate, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source, in a weight ratio of the microcrystalline cellulose to the surface-reacted calcium carbonate from 99.9:0.1 to 50:50, and
  b) co-processing the mixture obtained in step a) obtaining thereby the particulate pharmaceutical or nutraceutical excipient.

With regard to the definition of the excipient, surface-reacted calcium carbonate, microcrystalline cellulose and preferred embodiments thereof, reference is made to the statements provided above when discussing the technical details of the particulate pharmaceutical or nutraceutical excipient of the present invention.

In one embodiment, the process for the preparation of the particulate pharmaceutical or nutraceutical excipient consists of the steps of:
  a) mixing microcrystalline cellulose and surface-reacted calcium carbonate, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source, in a weight ratio of the microcrystalline cellulose to the surface-reacted calcium carbonate from 99.9:0.1 to 50:50, and
  b) co-processing the mixture obtained in step a) obtaining thereby the particulate pharmaceutical or nutraceutical excipient.

Step a) of mixing the microcrystalline cellulose with the surface-reacted calcium carbonate preferably takes place under mixing conditions in order to achieve a homogenous mixture of the mixing microcrystalline cellulose and surface-reacted calcium carbonate. The homogenous mixture is preferably such that the surface-reacted calcium carbonate is evenly distributed within the microcrystalline cellulose. The skilled man will adapt these mixing conditions (such as the configuration of mixing pallets and mixing speed) according to his process equipment.

In one embodiment, mixing step a) can be performed in that the microcrystalline cellulose and the surface-reacted calcium carbonate are mixed in a dry state.

Preferably, mixing step a) is performed in an aqueous medium such as to form an aqueous slurry comprising the microcrystalline cellulose and the surface-reacted calcium carbonate. This embodiment is advantageous as it specifically results in a homogenous mixture of the microcrystalline cellulose and surface-reacted calcium carbonate.

The aqueous slurry formed preferably has a solids content in the range from 5 to 80 wt.-%, based on the total weight of the aqueous slurry. According to a preferred embodiment the solids content of the aqueous slurry is in the range from 8 to 70 wt.-%, more preferably in the range from 8 to 60 wt.-% and most preferably in the range from 10 to 40 wt.-%, based on the total weight of the aqueous slurry.

The term "aqueous" slurry refers to a system, wherein the liquid phase comprises, preferably consists of, water. However, said term does not exclude that the liquid phase of the aqueous slurry comprises minor amounts of at least one water-miscible organic solvent selected from the group comprising methanol, ethanol, acetone, acetonitrile, tetrahydrofuran and mixtures thereof. If the aqueous slurry comprises at least one water-miscible organic solvent, the liquid phase of the aqueous slurry comprises the at least one water-miscible organic solvent in an amount of from 0.1 to 40.0 wt.-%, preferably from 0.1 to 30.0 wt.-%, more preferably from 0.1 to 20.0 wt.-% and most preferably from 0.1 to 10.0 wt.-%, based on the total weight of the liquid phase of the aqueous slurry. For example, the liquid phase of the aqueous slurry consists of water.

In a preferred embodiment, the aqueous slurry consists of water, the microcrystalline cellulose and the surface-reacted calcium carbonate.

It is appreciated that the surface-reacted calcium carbonate may be pre-activated by slight milling (or grinding) before subjected to process step a). That is to say, a pre-activated surface-reacted calcium carbonate can be subjected to process step a), i.e. mixed with the microcrystalline cellulose in process step a).

According to step b) of the present process, the mixture obtained in step a) is co-processed obtaining thereby the particulate pharmaceutical or nutraceutical excipient.

It is appreciated that the term "co-processing" or "co-processed" refers to a process step such that the surface-reacted calcium carbonate is in intimate association with the microcrystalline cellulose in the resulting excipient.

For example, co-processing step b) can be performed by a dry- or wet-processing. In particular, it is preferred that co-processing step b) is performed by high-shear mixing, spray drying, milling or mixtures thereof.

It is appreciated that the method used in step b) preferably depends on whether the mixture obtained in step a) is a dry mixture or an aqueous slurry of the surface-reacted calcium carbonate and the microcrystalline cellulose.

For example, if a dry mixture of the surface-reacted calcium carbonate and the microcrystalline cellulose is obtained in step a), co-processing step b) is preferably performed by dry-processing. In one embodiment, co-processing step b) is performed by high-shear mixing and/or milling, preferably high-shear mixing or milling, e.g. high-shear mixing.

High-shear mixing and milling are well known in the art and the skilled person will adapt the mixing or milling conditions (such as the configuration of mixing pallets and mixing speed) according to his process equipment. The mixing speed may be e.g in the range from 1000 to 3000 rpm. For example, a mixture of Somakon Verfahrenstechnik UG, Germany, may be used.

In one embodiment, the surface-reacted calcium carbonate may be slightly milled (or ground) and then mixed and co-processed with the microcrystalline cellulose by subjecting the mixture to a high-shear mixing.

If an aqueous slurry of the surface-reacted calcium carbonate and the microcrystalline cellulose is obtained in step a), co-processing step b) is preferably performed by spray-drying or milling, preferably spray-drying.

Preferably, the mixture obtained in step a) is in form of an aqueous slurry and co-processing step b) is performed by spray-drying.

Spray-drying is well known in the art and the skilled person will adapt the respective conditions (such as the spray pressure, inlet and outlet temperatures and pump) according to his process equipment.

In a preferred embodiment, the particulate pharmaceutical or nutraceutical excipient is prepared by a process comprising the steps of:
a) mixing microcrystalline cellulose and surface-reacted calcium carbonate, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source, in a weight ratio of the microcrystalline cellulose to the surface-reacted calcium carbonate from 99.9:0.1 to 50:50, and
b) co-processing the mixture obtained in step a) by spray drying obtaining thereby the particulate pharmaceutical or nutraceutical excipient.

According to a further aspect, the use of the particulate pharmaceutical or neutraceutical excipient for the manufacturing of a pharmaceutical or nutraceutical composition is provided.

With regard to the definition of the particulate pharmaceutical or nutraceutical excipient and preferred embodiments thereof, reference is made to the statements provided above when discussing the technical details of the particulate pharmaceutical or nutraceutical excipient of the present invention.

It is appreciated that the particulate pharmaceutical or neutraceutical excipient provides excellent flowability properties.

Thus, in a further aspect, the present invention refers to the use of co-processed microcrystalline cellulose and surface-reacted calcium carbonate for improving the flowability properties of an excipient.

Additionally or alternatively, the particulate pharmaceutical or neutraceutical excipient features a higher bulk density compared to the microcrystalline cellulose alone.

Thus, in a further aspect, the use of co-processed microcrystalline cellulose and surface-reacted calcium carbonate for increasing the loose bulk density of an excipient is provided. For example, the excipient has a loose bulk density from 0.25 to 0.90 g/ml, more preferably from 0.25 to 0.65 g/ml.

Pharmaceutical or Nutraceutical Composition

The present invention refers in another aspect to a pharmaceutical or nutraceutical composition comprising the particulate pharmaceutical or nutraceutical excipient and optionally at least one active ingredient.

With regard to the definition of the particulate pharmaceutical or nutraceutical excipient and preferred embodiments thereof, reference is made to the statements provided above when discussing the technical details of the particulate pharmaceutical or nutraceutical excipient of the present invention.

It is appreciated that the pharmaceutical or nutraceutical excipient may be loaded or mixed first with the at least one active ingredient before being manufactured to the pharmaceutical or nutraceutical composition. In this embodiment, the present invention thus refers to a pharmaceutical or nutraceutical composition comprising the particulate pharmaceutical or nutraceutical excipient and at least one active ingredient.

Alternatively, the pharmaceutical or nutraceutical excipient may be manufactured to the pharmaceutical or nutraceutical composition first. In this embodiment, the present invention thus refers to a pharmaceutical or nutraceutical composition consisting of the particulate pharmaceutical or nutraceutical excipient and optional adjuvant(s) used for preparing the composition, i.e. without the active ingredient. Subsequently, the pharmaceutical or nutraceutical composition consisting of the particulate pharmaceutical or nutraceutical excipient and optional adjuvant(s) may be further loaded with the active ingredient. In this embodiment, the present invention refers to a pharmaceutical or nutraceutical composition comprising the particulate pharmaceutical or nutraceutical excipient and at least one active ingredient and optional adjuvant(s).

The excipient is a superior agent to deliver active ingredients which are loaded onto or mixed with the excipient. Thus, generally, any agent is suitable to be transported by the excipient according to the invention. For example, active ingredients such as those selected from the group comprising pharmaceutically or nutraceutically active ingredients, inactive pharmaceutical or nutraceutical precursors, biologically active ingredients, inactive biological precursors and mixtures thereof. According to one embodiment, at least one active ingredient is associated with the excipient.

The term "active ingredient" in the meaning of the present invention refers to a substance having a specific effect in an organism and causing a specific reaction in humans, animals, microorganisms and/or plants.

It is appreciated that the active ingredient may be a chiral compound. Thus, active ingredient encompass the (R)-enantiomer, (S)-enantiomer and mixtures thereof, e.g. the racemic mixture.

Additionally or alternatively, the ingredients may be an isomeric compound. Thus, the active ingredient encompasses the (Z)-isomer, (E)-isomer and mixtures thereof.

Within the context of the present invention, an active ingredient encompasses also inactive pharmaceutical, nutraceutical and biological precursors which will be activated at a later stage.

The activation of such inactive precursors is known to the skilled person and commonly in use, e.g. activation in the stomach and/or gestro-interstinal pathway—such as acidic activation, tryptic—, chimotryptic or pepsinogenic cleavage.

It lies within the understanding of the skilled person that the mentioned activation methods are of mere illustrative character and are not intended to be of limiting character.

The pharmaceutically active ingredient or pharmaceutically inactive precursor thereof is preferably selected from the group comprising pharmaceutically active ingredients or pharmaceutically inactive precursor of synthetic origin, semi-synthetic origin, natural origin and combinations thereof.

Thus, a pharmaceutically active ingredient refers to pharmaceutically active ingredients which are of synthetic origin, semi-synthetic origin, natural origin and combinations thereof. Further, a pharmaceutically inactive precursor of the pharmaceutically active ingredient refers to pharmaceutically inactive precursor which are of synthetic origin, semi-synthetic origin, natural origin and combinations thereof and will be activated at a later stage to the respective pharmaceutically active ingredient.

It is to be noted that the pharmaceutically active ingredient or pharmaceutically inactive precursor thereof, may be any such compound known to the skilled person.

Pharmaceutically active ingredients thus include any compound that provides prophylactic and/or therapeutic properties when administered to humans and/or animals. Examples include, but are not limited to, pharmaceutical actives, therapeutic actives, veterinarian actives, and growth regulators.

The pharmaceutically active ingredient or pharmaceutically inactive precursor thereof can be an anti-inflammatory agent. Such agents may include, but are not limited to, non-steroidal anti-inflammatory agents or NSAIDs, such as propionic acid derivatives; acetic acid derivatives; fenamic acid derivatives; biphenylcarboxylic acid derivatives; and oxicams. All of these NSAIDs are fully described in U.S. Pat. No. 4,985,459 to Sunshine et al., incorporated by reference herein in its entirety as to the description of such NSAIDs. Examples of useful NSAIDs include acetylsalicylic acid, ibuprofen, naproxen, benoxaprofen, flurbiprofen, fenoprofen, fenbufen, ketoprofen, indoprofen, pirprofen, carprofen, oxaprozin, pranoprofen, microprofen, tioxaprofen, suprofen, alminoprofen, tiaprofenic acid, fluprofen, bucloxic acid and mixtures thereof.

Also useful are the steroidal anti-inflammatory drugs such as hydrocortisone and the like, and COX-2 inhibitors such as meloxicam, celecoxib, rofecoxib, valdecoxib, etoricoxib or mixtures thereof. Mixtures of any of the above anti-inflammatoires may be used.

Other materials that can be used as pharmaceutically active ingredient or pharmaceutically inactive precursor thereof include commonly known mouth and throat products. These products include, but are not limited to, upper respiratory agents such as phenylephrine, diphenhydramine, dextromethorphan, bromhexine and chlorpheniramine, gastrointestinal agents such as famotidine, loperamide and simethicone, anti-fungals such as miconazole nitrate, antibiotics and analgesics such as ketoprofen and fluributrofen.

The pharmaceutically active ingredient or pharmaceutically inactive precursor thereof may be also selected from sodium pyrosulphite, butylhydroxytoluene, butylated hydroxyanisole.

The pharmaceutically active ingredient or pharmaceutically inactive precursor thereof may be also selected from ephedrine, magaldrate, pseudoephedrine, sildenafil, xylocaine, benzalconium chloride, caffeine, phenylephrine, amfepramone, orlistat, sibutramine, acetaminophen, aspirin, glitazones, metformin, chlorpromazine, dimenhydrinat, domperidone, meclozine, metoclopramide, odansetron, prednisolone, promethazine, acrivastine, cetirizine, cinnarizine, clemastine, cyclizine, desloratadine, dexchlorpheniramine, dimenhydrinate, ebastine, fexofenadine, ibuprofen, levolevoproricin, loratadine, meclozine, mizolastine, promethazine, miconazole, chlorhexidine diacetate, fluoride, decapeptide KSL, aluminium fluoride, aminochelated calcium, ammonium fluoride, ammonium fluorosilicate, ammonium monofluorphosphate, calcium fluoride, calcium gluconate, calcium glycerophosphate, calcium lactate, calcium monofluorphosphate, calciumcarbonate, carbamide, cetyl pyridinium chloride, chlorhexidine, chlorhexidine digluconate, chlorhexidine chloride, chlorhexidine diacetate, CPP caseine phospho peptide, hexetedine, octadecentyl ammonium fluoride, potassium fluorosilicate, potassium chloride, potassium monofluorphosphate, sodium bi carbonate, sodium carbonate, sodium fluoride, sodium fluorosilicate, sodium monofluorphosphate, sodium tri polyphosphate, stannous fluoride, stearyl trihydroxyethyl propylenediamine dihydrofluoride, strontium chloride, tetra potassium pyrophosphate, tetra sodium pyrophosphate, tripotassium orthophosphate, trisodium orthophosphate, alginic acid, aluminium hydroxide, sodium bicarbonate, sildenafil, tadalafil, vardenafil, yohimbine, cimetidine, nizatidine, ranitidine, acetylsalicylic acid, clopidogrel, acetylcysteine, bromhexine, codeine, dextromethorphan, diphenhydramine, noscapine, phenylpropanolamine, vitamin D, simvastatin, bisacodyl, lactitol, lactulose, magnesium oxide, sodium picosulphate, senna glycosides, benzocaine, lidocaine, tetracaine, almotriptan, eletriptan, naratriptan, rizatriptan, sumatriptan, zolmitriptan, calcium, chromium, copper, iodine, magnesium, manganese, molybdenium, phosphor, selenium, zinc, chloramine, hydrogenperoxide, metronidazole, triamcinolonacetonide, benzethonium chl., cetyl pyrid. chl., chlorhexidine, fluoride, lidocaine, amphotericin, miconazole, nystatin, fish oil, *Ginkgo Biloba, ginseng*, ginger, purple coneflower, saw palmetto, cetirizine, levocetirizine, loratadine, diclofenac, flurbiprofen, acrivastine pseudoephedrine, loratadine pseudoephedrine, glucosamine, hyaluronic acid, decapeptide KSL-W, decapeptide KSL, resveratrol, misoprostol, bupropion, ondansetron HCl, esomeprazole, lansoprazole, omeprazole, pantoprazole, rabeprazole, bacteria and the like, loperamide, simethicone, acetylsalicylic acid and others, sucralfate, clotrimazole, fluconazole, itraconazole, ketoconazole, terbinafine, allopurinol, probenecid, atorvastatin, fluvastatin, lovastatin, nicotinic acid, pravastatin, rosuvastatin, simvastatin, pilocarpine, naproxen, alendronate, etidronate, raloxifene, risedronate, benzodiazepines, disulphiram, naltrexone, buprenorphine, codeine, dextropropoxyphene, fentanyl, hydromorphone, ketobemidone, ketoprofen, methadone, morphine, naproxen, nicomorphine, oxycodone, pethidine, tramadol, amoxicillin, ampicillin, azithromycin, ciprofloxacin, clarithromycin, doxycyclin, erythromycin, fusidic acid, lymecycline, metronidazole, moxifloxacin, ofloxacin, oxytetracycline, phenoxymethylpenicillin, rifamycins, roxithromycin, sulphamethizole, tetracycline, trimethoprim, vancomycin, acarbose, glibenclamide, gliclazide, glimepiride, glipizide, insulin, repaglinide, tolbutamide, oseltamivir, aciclovir, famciclovir, penciclovir, valganciclovir, amlopidine, diltiazem, felodipine, nifedipine, verapamil, finasteride, minoxidil, cocaine, buphrenorphin, clonidine, methadone, naltrexone, calcium antagonists, clonidine, ergotamine, β-blockers, aceclofenac, celecoxib, dexiprofen, etodolac, indometacin, ketoprofen, ketorolac, lornoxicam, meloxicam, nabumetone, oiroxicam, parecoxib, phenylbutazone, piroxicam, tiaprofenic acid, tolfenamic acid, aripiprazole, chlorpromazine, chlorprothixene, clozapine, flupentixol, fluphenazine, haloperidol, lithium carbonate, lithium citrate, melperone, penfluridol, periciazine, perphenazine, pimozide, pipamperone, prochlorperazine, risperidone, thioridizin, fluconazole, itraconazole, ketoconazole, voriconazole, opium, benzodiazepines, hydroxine, meprobamate, phenothiazine, aluminiumaminoacetate, esomeprazole, famotidine, magnesium oxide, nizatide, omeprazole, pantoprazole, fluconazole, itraconazole, ketoconazole, metronidazole, amphetamine, atenolol, bisoprolol fumarate, metoprolol, metropolol, pindolol, propranolol, auranofin, and bendazac.

Further examples of useful pharmaceutically active ingredients or pharmaceutically inactive precursors thereof can include active ingredients selected from the therapeutical groups comprising: Analgesic, Anaesthetic, Antipyretic, Anti-allergic, Anti-arrhythmic, Appetite suppressant, Antifungal, Anti-inflammatory, Broncho dilator, Cardiovascular drugs, Coronary dilator, Cerebral dilator, Peripheral vasodilator, Anti-infective, Psychotropic, Anti-manic, Stimulant, Antihistamine, Laxative, Decongestant, Gastro-intestinal sedative, Sexual dysfunction agent, Disinfectants, Anti-diarrhoeal, Anti-anginal substance, Vasodilator, Anti-hypertensive agent, Vasoconstrictor, Migraine treating agent, Antibiotic, Tranquilizer, Antipsychotic, Anti-tumour drug, Anticoagulant, Antithrombotic agent, Hypnotic, Sedative, Anti-emetic, Anti-nauseant, Anticonvulsant, Neuromuscular agent, Hyper and hypoglycaemic, Thyroid and antithyroid, Diuretic, Antispasmodic, Uterine relaxant, Anti-obesity agent, Anorectic, Spasnolytics, Anabolic agent, Erythropoietic agent, Anti-asthmatic, Expectorant, Cough suppressant, Mucolytic, Anti-uricemic agent, Dental vehicle, Breath freshener, Antacid, Anti-diuretic, Anti-flatulent, Beta-blocker, Teeth Whitener, Enzyme, Co-enzyme, Protein, Energy booster, Fibre, Probiotics, Prebiotics, NSAID, Anti-tussives, Decongestants, Anti-histamines, Expectorants, Anti-diarrhoeals, Hydrogen antagonists, Proton pump inhibitors, General nonselective CNS depressants, General nonselective CNS stimulants, Selectively CNS function modifying drugs, Antiparkinsonism, Narcotic-analgetics, Analgetic-antipyretics, Psychopharmacological drugs, and Sexual dysfunction agents.

Examples of useful pharmaceutically active ingredients or pharmaceutically inactive precursors thereof may also include: Casein glyco-macro-peptide (CGMP), Triclosan, Cetyl pyridinium chloride, Domiphen bromide, Quaternary ammonium salts, zinc components, Sanguinarine, Fluorides, Alexidine, Octonidine, EDTA, Aspirin, Acetaminophen, Ibuprofen, Ketoprofen, Diflunisal, Fenoprofen calcium, Naproxen, Tolmetin sodium, Indomethacin, Benzonatate, Caramiphen edisylate, Menthol, Dextromethorphan hydrobromide, Theobromine hydrochloride, Chlophendianol Hydrochloride, Pseudoephedrine Hydrochloride, Phenylephrine, Phenylpropanolamine, Pseudoephedrine sulphate, Brompheniramine maleate, Chlorpheniraminemaleate, Carbinoxamine maleate, Clemastine fumarate, Dexchlorpheniramine maleate, Dephenhydramine hydrochloride, Diphenpyralide hydrochloride, Azatadine maleate, Diphenhydramine citrate, Doxylamine succinate, Promethazine hydrochloride, Pyrilamine maleate, Tripellenamine citrate, Triprolidine hydrochloride, Acrivastine, Loratadine, Brompheniramine, Dexbrompheniramine, Guaifenesin, Ipecac, potassium iodide, Terpin hydrate, Loperamide, Famotidine, Ranitidine, Omeprazole, Lansoprazole, Aliphatic alcohols, Barbiturates, caffeine, strychnine, Picrotoxin, Pentyenetetrazol, Phenyhydantoin, Phenobarbital, Primidone, Carbamazapine, Etoxsuximide, Methsuximide, Phensuximide, Trimethadione, Diazepam, Benzodiazepines, Phenacemide, Pheneturide, Acetazolamide, Sulthiame, bromide, Levodopa, Amantadine, Morphine, Heroin, Hydromorphone, Metopon, Oxymorphone, Levophanol, Codeine, Hydrocodone, Xycodone, Nalorphine, Naloxone, Naltrexone, Salicylates, Phenylbutazone, Indomethacin, Phenacetin, Chlorpromazine, Methotrimeprazine, Haloperidol, Clozapine, Reserpine, Imipramine, Tranylcypromine, Phenelzine, Lithium, Sildenafil citrate, Tadalafil, and Vardenafil CL. For example, eugenol can be used as anaesthetic.

Examples of useful pharmaceutically active ingredients or pharmaceutically inactive precursor thereof may include active ingredients selected from the groups of ace-inhibitors, antianginal drugs, anti-arrhythmias, anti-asthmatics, anti-cholesterolemics, analgesics, anaesthetics, anticonvulsants, anti-depressants, anti-diabetic agents, anti-diarrhoea preparations, antidotes, anti-histamines, anti-hypertensive drugs, anti-inflammatory agents, anti-lipid agents, anti-manics, anti-nauseants, anti-stroke agents, anti-thyroid preparations, anti-tumour drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplasties, antiparkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies such as sildenafil citrate, which is currently marketed as Viagra™, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids such as bromocriptine, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumour drugs, anti-coagulants, anti-thrombotic drugs, hypnotics, anti-emetics, anti-nauseants, anticonvulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof.

Examples of useful pharmaceutically active ingredients or pharmaceutically inactive precursors thereof contemplated can also include antacids, $H_2$-antagonists, and analgesics. For example, antacid dosages can be prepared using the ingredients calcium carbonate alone or in combination with magnesium hydroxide, and/or aluminium hydroxide. Moreover, antacids can be used in combination with $H_2$-antagonists.

Analgesics include opiates and opiate derivatives, such as Oxycontin™, ibuprofen, aspirin, acetaminophen, and combinations thereof that may optionally include caffeine.

Other useful pharmaceutically active ingredients or pharmaceutically inactive precursors thereof can include anti-diarrhoeals such as Immodium™ AD, anti-histamines, anti-tussives, decongestants, vitamins, and breath fresheners. Also contemplated for use herein are anxiolytics such as Xanax™; anti-psychotics such as Clozaril™ and Haldol™; non-steroidal anti-inflammatoires (NSAID's) such as ibuprofen, naproxen sodium, Voltaren™ and Lodine™, anti-histamines such as Claritin™, Hismanal™, Relafen™, and Tavist™; antiemetics such as Kytril™ and Cesamet™; bronchodilators such as Bentolin™, Proventil™; anti-depressants such as Prozac™, Zoloft™, and Paxil™; anti-migraines such as Imigra™, ACE-inhibitors such as Vasotec™, Capoten™ and Zestril™; anti-Alzheimer's agents, such as Nicergoline™; and CaH-antagonists such as Procardia™, Adalat™, and Calan™.

The popular $H_2$-antagonists which are contemplated for use in the present invention include cimetidine, ranitidine hydrochloride, famotidine, nizatidine, ebrotidine, mifentidine, roxatidine, pisatidine and aceroxatidine.

Active antacid ingredients can include, but are not limited to, the following: aluminium hydroxide, dihydroxyaluminium aminoacetate, aminoacetic acid, aluminium phosphate, dihydroxyaluminium sodium carbonate, bicarbonate, bismuth aluminate, bismuth carbonate, bismuth subcarbonate, bismuth subgallate, bismuth subnitrate, bismuth subsilysilate, calcium phosphate, citrate ion (acid or salt), amino acetic acid, hydrate magnesium aluminate sulphate, magaldrate, magnesium aluminosilicate, magnesium carbonate, magnesium glycinate, magnesium hydroxide, magnesium oxide, magnesium trisilicate, milk solids, aluminium mono-ordibasic calcium phosphate, tricalcium phosphate, potassium bicarbonate, sodium tartrate, sodium bicarbonate, magnesium aluminosilicates, tartaric acids and salts.

In some embodiments, the pharmaceutically active ingredient or pharmaceutically inactive precursor thereof can be selected from analgesics/anaesthetics such as menthol, phenol, hexylresorcinol, benzocaine, dyclonine hydrochloride, benzyl alcohol, salicyl alcohol, and combinations thereof. In some embodiments, the pharmaceutically active ingredient or pharmaceutically inactive precursor thereof can be selected from demulcents such as slippery elm bark, pectin, gelatin, and combinations thereof. In some embodiments, the pharmaceutically active ingredient or pharmaceutically inactive precursor thereof can be selected from antiseptic ingredients such as cetylpyridinium chloride, domiphen bromide, dequalinium chloride, eugenol and combinations thereof.

In some embodiments, the pharmaceutically active ingredient or pharmaceutically inactive precursor thereof can be selected from antitussive ingredients such as chlophedianol hydrochloride, codeine, codeine phosphate, codeine sulphate, dextromethorphan, dextromethorphan hydrobromide, diphenhydramine citrate, and diphenhydramine hydrochloride, and combinations thereof.

In some embodiments, the pharmaceutically active ingredient or pharmaceutically inactive precursor thereof can be selected from throat soothing agents such as honey, propolis, aloe vera, glycerine, menthol and combinations thereof. In still other embodiments, the pharmaceutically active ingredient or pharmaceutically inactive precursor thereof can be selected from cough suppressants. Such cough suppressants can fall into two groups: those that alter the texture or production of phlegm such as mucolytics and expectorants; and those that suppress the coughing reflex such as codeine (narcotic cough suppressants), antihistamines, dextromethorphan and isoproterenol (non-narcotic cough suppressants).

In still other embodiments, the pharmaceutically active ingredient or pharmaceutically inactive precursor thereof can be an antitussive selected from the group comprising codeine, dextromethorphan, dextrorphan, diphenhydramine, hydrocodone, noscapine, oxycodone, pentoxyverine and combinations thereof. In some embodiments, the pharmaceutically active ingredient or pharmaceutically inactive precursor thereof can be selected from antihistamines such as acrivastine, azatadine, brompheniramine, chlo[phi]heniramine, clemastine, cyproheptadine, dexbrompheniramine, dimenhydrinate, diphenhydramine, doxylamine, hydroxyzine, meclizine, phenindamine, phenyltoloxamine, promethazine, pyrilamine, tripelennamine, triprolidine and combinations thereof. In some embodiments, the pharmaceutically active ingredient or pharmaceutically inactive precursor thereof can be selected from non-sedating antihistamines such as astemizole, cetirizine, ebastine, fexofenadine, loratidine, terfenadine, and combinations thereof.

The nutraceutically active ingredient or nutraceutically inactive precursor thereof is preferably selected from the group comprising nutraceutically active ingredients or nutraceutically inactive precursor of synthetic origin, semi-synthetic origin, natural origin and combinations thereof.

Thus, a nutraceutically active ingredient refers to nutraceutically active ingredients which are of synthetic origin, semi-synthetic origin, natural origin and combinations thereof. Further, a nutraceutically inactive precursor of the nutraceutically active ingredient refers to nutraceutically inactive precursors which are of synthetic origin, semi-synthetic origin, natural origin and combinations thereof and will be activated at a later stage to the respective nutraceutically active ingredient.

It is to be noted that the nutraceutically active ingredient or nutraceutically inactive precursor thereof, may be any such compound known to the skilled person.

Nutraceutically active ingredients preferably include any compound that provides prophylactic and/or therapeutic properties when administered to humans and/or animals. It is appreciated that nutraceutically active ingredients may have the same effects and may encompass the same compounds as pharmaceutically active ingredients. However, dietary supplements and food additives are typically considered as nutraceutically active ingredients. Examples of nutraceutically active ingredients include, but are not limited to, vitamins, minerals, phytochemicals, probiotics, prebiotics and other substances such as curcumine, resveratrol and isoflavones.

For example, vitamin A, vitamin B1, vitamin B6, vitamin B12, vitamin B2, vitamin B6, vitamin D, vitamin E, i.e. tocopheroles, vitamin K, thiamine, riboflavin, biotin, folic acid, niacin, pantothenic acid, Q10, alpha lipoic acid, dihydrolipoic acid, curcumin, xanthophylls, beta cryptoxanthin, lycopene, lutein, zeaxanthin, astaxanthin, beta-carotene, carotenes, mixed carotenoids, polyphenols, flavonoids, sodium, potassium, calcium, magnesium, sulphur, chlorine, choline, and/or phytochemicals such as carotenoids, chlorophyll, chlorophyllin, fibre, flavanoids, anthocyanins, cyaniding, delphinidin, malvidin, pelargonidin, peonidin, petunidin, flavanols, catechin, epicatechin, epigallocatechin, epigallocatechingallate, theaflavins, thearubigins, proanthocyanins, flavonols, quercetin, kaempferol, myricetin, isorhamnetin, flavononeshesperetin, naringenin, eriodictyol, tangeretin, flavones, apigenin, luteolin, lignans, phytoestrogens, resveratrol, isoflavones, daidzein, genistein, glycitein, soy isoflavones, and combinations thereof, may be used. Examples of nutraceuticals that can be used as active ingredient(s) are set forth in U.S. Patent Application Publication Nos. 2003/0157213 A1, 2003/0206993 and 2003/0099741 A1 which are incorporated in their entirety herein by reference for all purposes.

In one embodiment, minerals, preferably trace minerals, can be used, e.g. manganese, zinc, copper, fluorine, molybdenum, iodine, cobalt, chromium, selenium, phosphorous, and combinations thereof.

It is appreciated that the pharmaceutical or nutraceutical composition comprises the at least one active ingredient preferably in an amount ranging from 0.1 to 99 wt.-%, more preferably from 0.2 to 60 wt.-%, and most preferably from 0.2 to 50 wt.-%, based on the total weight of the composition.

The pharmaceutical or nutraceutical composition of the present invention may further comprise at least one adjuvant selected from the group comprising natural or synthetic scenting agents, natural or synthetic flavoring agents, natural or synthetic coloring agents, natural or synthetic sweeteners, lubricants, disintegrants, glidants, and mixtures thereof.

Suitable natural or synthetic scenting agents include one or more volatilized chemical compounds, generally at a very low concentration, that humans or other animals perceive by the sense of olfaction.

Suitable natural or synthetic flavoring agents include but are not limited to mints, such as peppermint, menthol, vanilla, cinnamon, various fruit flavors, both individual or mixed, essential oils such as thymol, eucalyptol, menthol, and methyl salicylate, allylpyrazine, methoxypyrazines, 2-isobutyl-3 methoxypyrazine, acetyl-L-pyrazines, 2-acetoxy pyrazine, aldehydes, alcohols, esters, ketones, pyrazines, phenolics, terpenoids and mixtures thereof.

The flavoring agents are generally utilized in amounts that will vary depending upon the individual flavor, and may, for example, range in amount of about 0.5% to about 4% by weight of the final composition.

Suitable natural or synthetic coloring agents include, but are not limited to, titanium dioxide, flavone dyes, isoquinoline dyes, polyene colorants, pyran colorants, naphthochinone dyes, chinone and anthrachinone dyes, chromene dyes, benzophyrone dyes as well as indigoid dyes and indole colorants. Examples thereof are caramel coloring, annatto, chlorophyllin, cochineal, betanin, turmeric, saffron, paprika, lycopene, pandan and butterfly pea.

Suitable natural or synthetic sweeteners include but are not limited to xylose, ribose, glucose, mannose, galactose, fructose, dextrose, sucrose, sugar, maltose, partially hydrolyzed starch, or corn syrup solid, and sugar alcohols such as sorbitol, xylitol, mannitol, and mixtures thereof; water soluble artificial sweeteners such as the soluble saccharin salts, i.e. sodium, or calcium saccharin salts, cyclamate salts, acesulfam-K and the like, and the free acid form of saccharin and aspartame based sweeteners such as L-aspartyl-phenylalanine methyl ester, Alitame® or Neotame®.

In general, the amount of sweetener will vary with the desired amount of sweeteners selected for a particular tablet composition.

In order to promote rapid disintegration of the pharmaceutical or nutraceutical composition disintegrants may be used. Such disintegrants are known to the skilled person as well as their mechanisms of action.

If a disintegrant is present, the pharmaceutical or nutraceutical composition according to the present invention preferably comprises a disintegrant selected form the group comprising modified cellulose gums, insoluble cross-linked polyvinylpyrrolidones, starch glycolates, micro crystalline cellulose, pregelatinized starch, sodium carboxymethyl starch, low-substituted hydroxypropyl cellulose, homopolymers of N-vinyl-2-pyrrolidone, alkyl-, hydroxyalkyl-, carboxyalkyl-cellulose esters, alginates, ion exchange resins, gums, chitin, chitosan, clays, gellan gum, crosslinked polacrillin copolymers, agar, gelatine, dextrines, acrylic acid polymers, carboxymethylcellulose sodium/calcium, hydroxypropyl methyl cellulose phtalate, shellac or mixtures thereof.

Suitable lubricants include but are not limited to talc, silica, fats such as vegetable stearin, magnesium stearate, sodium stearyl fumarate or stearic acid.

Suitable glidants include but are not limited to talc, fumed silica or magnesium carbonate.

It is appreciated that the at least one adjuvant is preferably present in the pharmaceutical or nutraceutical composition in an amount ranging from 0.1 to 20 wt.-%, more preferably from 0.2 to 7 wt.-%, based on the total weight of the composition.

In one embodiment, the pharmaceutical or nutraceutical composition comprises, preferably consists of the particulate pharmaceutical or nutraceutical excipient, an active ingredient and a lubricant as the at least one adjuvant.

According to a further aspect, a process for manufacturing the pharmaceutical or nutraceutical composition is provided. The process comprises the steps of:
a) providing a particulate pharmaceutical or nutraceutical excipient,
b) subjecting the particulate pharmaceutical or nutraceutical excipient to dry granulation, wet granulation, melt granulation or direct compression, preferably direct compression, obtaining thereby the composition.

With regard to the definition of the particulate pharmaceutical or nutraceutical excipient and preferred embodiments thereof, reference is made to the statements provided above when discussing the technical details of the particulate pharmaceutical or nutraceutical excipient of the present invention.

In one embodiment, the process further comprises a step c) of contacting the particulate pharmaceutical or nutraceutical excipient before step b) or the composition obtained in step b) with at least one active ingredient. Preferably, the process further comprises a step c) of contacting the particulate pharmaceutical or nutraceutical excipient before step b) with at least one active ingredient.

It is appreciated that at least one active ingredient is selected from the group comprising pharmaceutically or nutraceutically active ingredients, inactive pharmaceutical or nutraceutical precursors, biologically active ingredients, inactive biological precursors and mixtures thereof, and/or at least one adjuvant selected from the group comprising natural or synthetic scenting agents, natural or synthetic flavoring agents, natural or synthetic coloring agents, natural or synthetic sweeteners, lubricants, disintegrants, glidants, and mixtures thereof.

It is appreciated that the pharmaceutical or nutraceutical "composition" specifically refers to a solid pharmaceutical or nutraceutical drug product containing excipients and active ingredients in a particular configuration and dose. Such compositions are well known and typically used in pharmaceutical or nutraceutical applications, such as a tablet. The composition, preferably tablet, may be in any shape and size known in the art.

In view of the foregoing, the pharmaceutical or nutraceutical composition can be formed by any technique known by the skilled person resulting in the shape of a tablet.

According to step b), the particulate pharmaceutical or nutraceutical excipient is thus subjected to dry granulation, wet granulation, melt granulation or direct compression obtaining thereby the composition.

In one embodiment, the particulate pharmaceutical or nutraceutical excipient is subjected to dry granulation to form the composition. In this case, the particles of the particulate pharmaceutical or nutraceutical excipient are compacted/granulated in dry conditions under high pressure. Methods and equipments for dry granulation are well known in the art and the skilled person will adapt the dry granulation conditions accordingly. For example, dry granulation can be carried out through a sweying granulator or a roller compactor.

In an alternative embodiment, the particulate pharmaceutical or nutraceutical excipient is subjected to wet granulation, e.g. by high-shear mixing or fluidized bed granulation, to form the composition. In this case, the composition is formed by adding a granulation liquid onto a bed of the particulate pharmaceutical or nutraceutical excipient which is under the influence of an impeller screw or air. An agitation resulting in the system together with the wetting of the excipient results in its aggregation. Methods and equipments for wet granulation are well known in the art and the skilled person will adapt the wet granulation conditions accordingly.

In an alternative embodiment, the particulate pharmaceutical or nutraceutical excipient is subjected to melt granulation to form the composition. In this case, the composition is formed by combining the particulate pharmaceutical or nutraceutical excipient with a binder that melts or softens at relatively low temperatures (about 40 to 80° C.) to achieve agglomeration of the excipient. Methods and equipments for melt granulation are well known in the art and the skilled person will adapt the melt granulation conditions accordingly.

If the particulate pharmaceutical or nutraceutical excipient is subjected to dry granulation, wet granulation or melt granulation to form the composition, it is appreciated that the weight ratio of the microcrystalline cellulose (MCC) to the surface-reacted calcium carbonate (SRCC) may be from 99.9:0.1 to 10:90, preferably from 99.9:0.1 to 25:75.

In one embodiment, the particulate pharmaceutical or nutraceutical excipient is subjected to a direct compression to form the composition. In this case, the composition is formed by directly compressing the particulate pharmaceutical or nutraceutical excipient, which is typically pre-loaded or mixed with the at least one active ingredient. Methods and equipments for direct compression are well known in the art and the skilled person will adapt the direct compression conditions accordingly.

Preferably, the composition is formed by direct compression.

In one embodiment, the process for manufacturing the pharmaceutical or nutraceutical composition comprises the steps of:
a) providing the particulate pharmaceutical or nutraceutical excipient which is prepared by a process comprising the steps of:
i) mixing microcrystalline cellulose and surface-reacted calcium carbonate, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source, in a weight ratio of the microcrystalline cellulose to the surface-reacted calcium carbonate from 99.9:0.1 to 50:50, and
ii) co-processing the mixture obtained in step a) by spray drying obtaining thereby the particulate pharmaceutical or nutraceutical excipient, and
b) subjecting the particulate pharmaceutical or nutraceutical excipient to direct compression obtaining thereby the composition.

In one embodiment, the process for manufacturing the pharmaceutical or nutraceutical composition comprises the steps of:
  a) providing the particulate pharmaceutical or nutraceutical excipient which is prepared by a process comprising the steps of:
    i) mixing microcrystalline cellulose and surface-reacted calcium carbonate, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source, in a weight ratio of the microcrystalline cellulose to the surface-reacted calcium carbonate from 99.9:0.1 to 50:50, and
    ii) co-processing the mixture obtained in step a) by spray drying obtaining thereby the particulate pharmaceutical or nutraceutical excipient,
  b) subjecting the particulate pharmaceutical or nutraceutical excipient to direct compression obtaining thereby the composition, and
  c) contacting the particulate pharmaceutical or nutraceutical excipient before step b) with at least one active ingredient.

Figure 1:
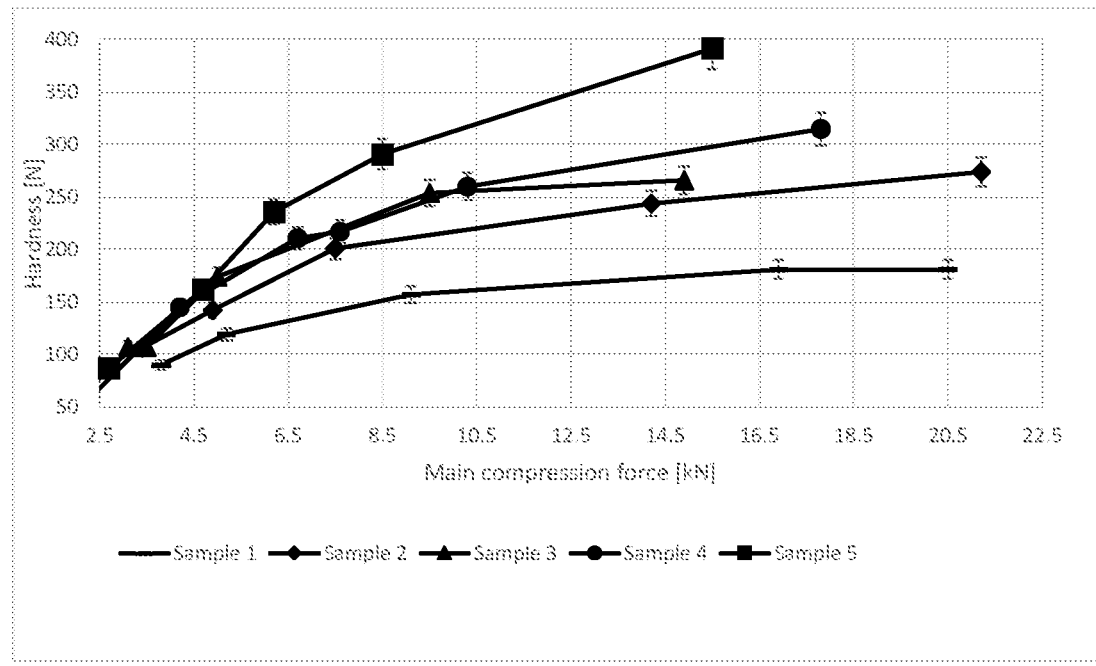
FIG. 1 shows the tablet hardness [N] of the excipients as a function of the main compression force [kN].

The following examples and tests will illustrate the present invention, but are not intended to limit the invention in any way.

EXAMPLES

Measurement Methods

In the following, measurement methods implemented in the examples are described.

Particle Size Distribution

Volume determined median particle size $d_{50}(vol)$ and the volume determined top cut particle size $d_{98}(vol)$ was evaluated using a Malvern Mastersizer 3000 Laser Diffraction System (Malvern Instruments Plc., Great Britain). The $d_{50}(vol)$ or $d_{98}(vol)$ value indicates a diameter value such that 50% or 98% by volume, respectively, of the particles have a diameter of less than this value. The raw data obtained by the measurement was analyzed using the Mie theory, with a particle refractive index of 1.57 and an absorption index of 0.005. The methods and instruments are known to the skilled person and are commonly used to determine particle size distributions of fillers and pigments. The sample was measured in dry condition without any prior treatment.

The weight determined median particle size $d_{50}(wt)$ was measured by the sedimentation method, which is an analysis of sedimentation behaviour in a gravimetric field. The measurement was made with a Sedigraph™ 5120 of Micromeritics Instrument Corporation, USA. The method and the instrument are known to the skilled person and are commonly used to determine particle size distributions of fillers and pigments. The measurement was carried out in an aqueous solution of 0.1 wt.-% $Na_4P_2O_7$. The samples were dispersed using a high speed stirrer and supersonicated.

Specific Surface Area (SSA)

The specific surface area was measured via the BET method according to ISO 9277:2010 using nitrogen, following conditioning of the sample by heating at 250° C. for a period of 30 minutes. Prior to such measurements, the sample was filtered within a Büchner funnel, rinsed with deionised water and dried at 110° C. in an oven for at least 12 hours.

Intra-Particle Intruded Specific Pore Volume (in cm3/g)

The specific pore volume was measured using a mercury intrusion porosimetry measurement using a Micromeritics Autopore V 9620 mercury porosimeter having a maximum applied pressure of mercury 414 MPa (60000 psi), equivalent to a Laplace throat diameter of 0.004 μm (~nm). The equilibration time used at each pressure step was 20 seconds. The sample material was sealed in a 5 cm³ chamber powder penetrometer for analysis. The data were corrected for mercury compression, penetrometer expansion and sample material compression using the software Pore-Comp (Gane, P. A. C., Kettle, J. P., Matthews, G. P. and Ridgway, C. J., "Void Space Structure of Compressible Polymer Spheres and Consolidated Calcium Carbonate Paper-Coating Formulations", Industrial and Engineering Chemistry Research, 35(5), 1996, p1753-1764).

The total pore volume seen in the cumulative intrusion data can be separated into two regions with the intrusion data from 214 μm down to about 1-4 μm showing the coarse packing of the sample between any agglomerate structures contributing strongly. Below these diameters lies the fine inter-particle packing of the particles themselves. If they also have intra-particle pores, then this region appears bi-modal, and by taking the specific pore volume intruded by mercury into pores finer than the modal turning point, i.e. finer than the bi-modal point of inflection, the specific intra-particle pore volume is defined. The sum of these three regions gives the total overall pore volume of the powder, but depends strongly on the original sample compaction/settling of the powder at the coarse pore end of the distribution.

By taking the first derivative of the cumulative intrusion curve the pore size distributions based on equivalent Laplace diameter, inevitably including pore-shielding, are revealed. The differential curves clearly show the coarse agglomerate pore structure region, the inter-particle pore region and the intra-particle pore region, if present. Knowing the intra-particle pore diameter range it is possible to subtract the remainder inter-particle and inter-agglomerate pore volume from the total pore volume to deliver the desired pore volume of the internal pores alone in terms of the pore volume per unit mass (specific pore volume). The same principle of subtraction, of course, applies for isolating any of the other pore size regions of interest.

Bulk Density

100±0.5 g of the respective material were carefully filled through a powder funnel into the 250 mL measuring cylinder and the volume was read off to the nearest 1 mL. The loose bulk density was the calculated according the formula:

Loose bulk density[g/mL]=bulk volume[mL]/weighed sample[g]

and the result was recorded to the nearest 0.01 g/mL.

Tapped Density

100±0.5 g of the respective material were carefully filled through a powder funnel into the 250 mL measuring cylinder.

The graduated cylinder is connected to a support provided with a settling apparatus capable of producing taps. The cylinder is secured in this support and the volume after 1250 taps is read. A subsequent second tapping step consisting of 1250 taps is performed and the value of the volume is read. When this second tapped volume value does not differ in more than 2 mL from this first tapped volume value, this is the tapped volume. When this value differs in more than 2 mL, the tapping step of 1250 taps is repeated until no differences of more than 2 mL in subsequent steps is observed.

Hausner Ratio

The Hausner ratio is a number that is correlated to the flowability of a powder material and is calculated as follows:

Hausner Ratio=(Tapped density)/(Bulk density)

Compressibility Index

The compressibility index is calculated as follows:

Compressibility Index (%)=(Tapped density−Bulk density)/Tapped density*100

Angle of Repose

Figure 13:
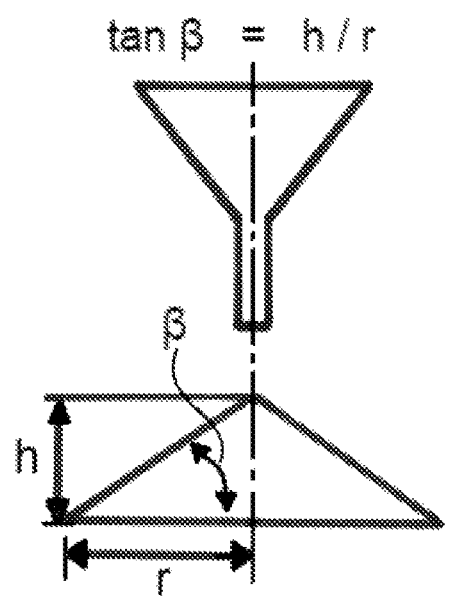
FIG. 13 shows a means for calculating the angle of repose (β) of a granulate bevel having a height (h) and radius (r), with the granulate bevel being formed by emptying granulate material through a hopper.

The angle of repose is measured in a flowability tester. The hopper equipped with the 10 mm nozzle is filled with approximately 150 mL of the respective material. After emptying the hopper, the granulate bevel is measured by means of a laser beam and the angle of repose is calculated. The angle of repose β is the angle of the bevel flank opposite the horizontal line that is calculated as shown in FIG. 13.

SEM

Samples for SEM investigation were prepared by filtering the suspensions and letting them dry in a drying oven at 110° C. The samples were sputtered with 20 nm gold before taking the pictures.

1. Pigment Materials

Microcrystalline Cellulose

Microcrystalline cellulose Avicel® PH 102 from FMC BioPolymer, Ireland was used.

Surface-Reacted Calcium Carbonate

SRCC

Surface-reacted calcium carbonate (SRCC) ($d_{50}$(vol)=6.6 μm, $d_{98=13.7}$ μm, SSA=59.9 m$^2$/g). The intra-particle intruded specific pore volume is 0.939 cm$^3$/g (for the pore diameter range of 0.004 to 0.51 μm).

SRCC was obtained by preparing 350 litres of an aqueous suspension of ground calcium carbonate in a mixing vessel by adjusting the solids content of a ground limestone calcium carbonate from Omya SAS, Orgon having a weight based median particle size $d_{50}$(wt) of 1.3 μm, as determined by sedimentation, such that a solids content of 10 wt.-%, based on the total weight of the aqueous suspension, is obtained.

Whilst mixing the slurry at a speed of 6.2 m/s, 11.2 kg phosphoric acid was added in form of an aqueous solution containing 30 wt.-% phosphoric acid to said suspension over a period of 20 minutes at a temperature of 70° C. After the addition of the acid, the slurry was stirred for additional 5 minutes, before removing it from the vessel and drying using a jet-dryer.

Ground Calcium Carbonate (GCC)

The ground calcium carbonate (GCC) was a ground limestone from Orgon, France, having a $d_{50}$(wt.)=3 μm, a $d_{98=12}$ μm, and a SSA=2.6 m$^2$/g.

2. Co-Processing Experiments to Prepare Excipients

A. Spray Drying

Spray-drying trials were performed on a Niro spray-dryer, Mobile Minor, using a pressure nozzle with the following settings:

Inlet temp: 240° C.

Outlet temp.: 95° C.

Spray pressure: 55%

Pump rpm: 22.3 ml/min

Nozzle orifice: 1 mm

Aqueous slurries of mixtures of microcrystalline cellulose (MCC) and surface-reacted calcium carbonate (SRCC) with different proportions were used for the spray drying experiments resulting in the preparation of the excipients. The aqueous slurries featured solids contents of 15 wt.-%, based on the total weight of the slurry.

Table 1 shows proportions of microcrystalline cellulose (MCC) to surface-reacted calcium carbonate (SRCC) that have been used to prepare the excipients:

TABLE 1

Proportions of MCC to SRCC

| Sample No. | Microcrystalline cellulose (MCC) (%) | Surface-reacted calcium carbonate (SRCC) (%) |
|---|---|---|
| 1 | 100 | 0 |
| 2 | 98 | 2 |
| 3 | 95 | 5 |
| 4 | 90 | 10 |
| 5 | 75 | 25 |

The density and compressibility values of the obtained co-processed excipients are listed in Table 2.

TABLE 2

Density and compressibility values

| Sample No. | Bulk density [g/ml] | Tapped density [g/ml] | Hausner Ratio | Acc. Ph | Angle of repose [°] | Acc. Ph |
|---|---|---|---|---|---|---|
| 1 | 0.36 | 0.49 | 1.36 | Poor | 41.1 | Fair |
| 2 | 0.39 | 0.53 | 1.36 | Poor | 42.5 | Passable |
| 3 | 0.41 | 0.52 | 1.27 | Fair | 39.7 | Fair |
| 4 | 0.39 | 0.51 | 1.31 | Passable | 39.0 | Fair |

Tabletting Assays of Co-Processed Compounds (Samples 1 to 4)

The obtained excipients (Samples 1 to 4) were further mixed with 0.5 wt.-% lubricant (Magnesium stearate, Ligamed MF-2-V, Cas #557-04-0, Peter Greven) in a Turbula Mixer (Willy A. Bachofen, Turbula T10B) for 5 minutes. The mix was further used to prepare tablets in a Fette 1200i using EU1" tooling, a 10 mm fill cam, 8 standard convex round 10 mm punches and a tableting speed of 15000 tablets/hour. The fill depth was adjusted to obtain compression forces of 2 kN up to 20 kN and the tablet weight was fixed at 175 mg.

Figure 2:
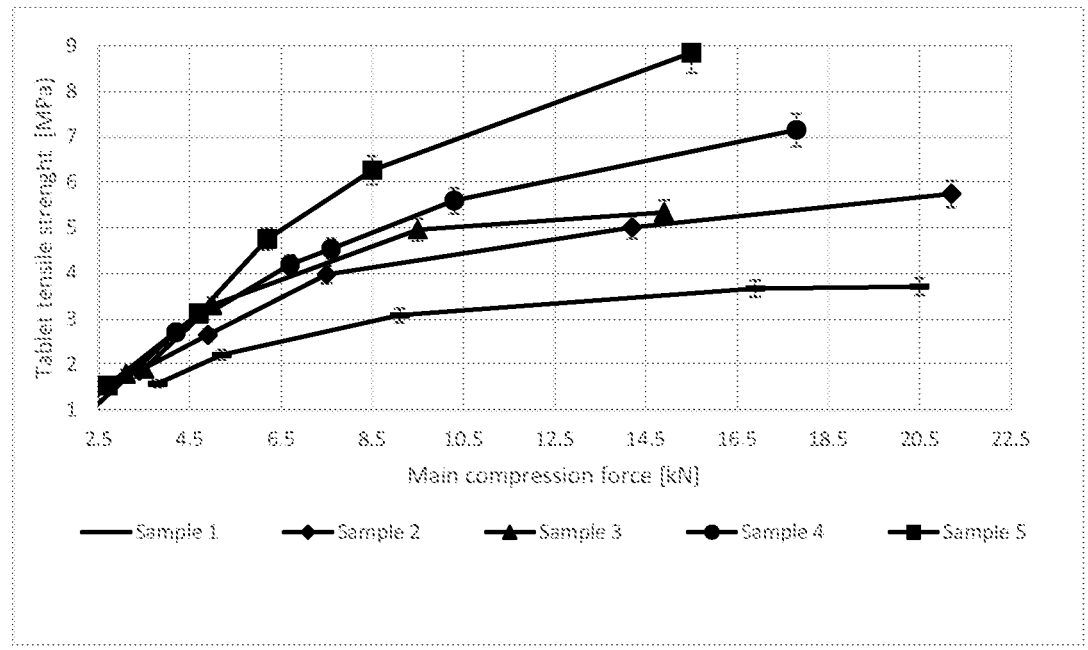
FIG. 2 shows the tablet tensile strength [MPa] of the co-processed compounds as a function of the main compression force [kN].
Figure 3:
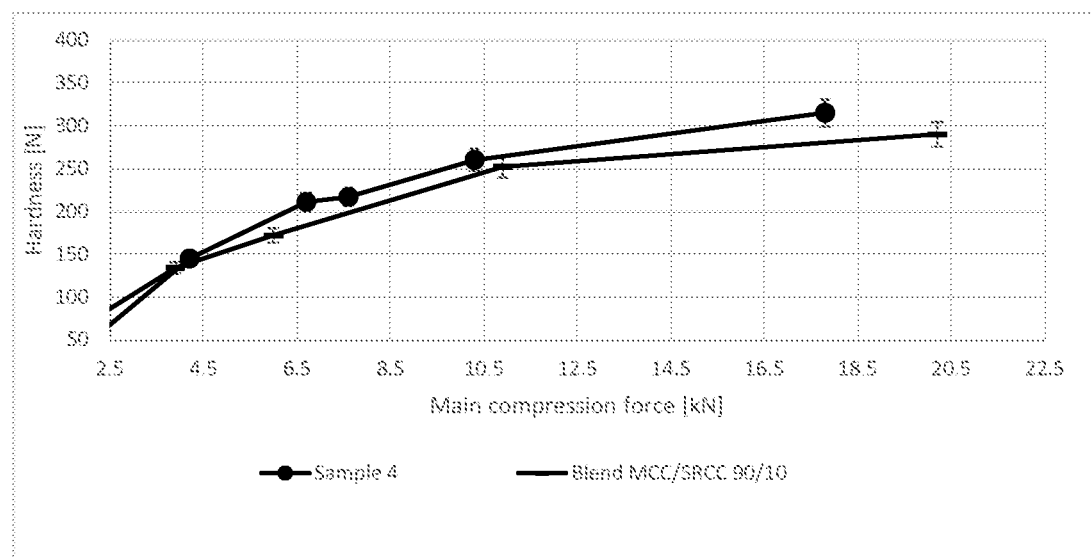
FIG. 3 shows a comparison of the tablet hardness [N] as a function of the main compression force [kN] for Sample 4 as well as for a simple blend of MCC and SRCC.
Figure 4:
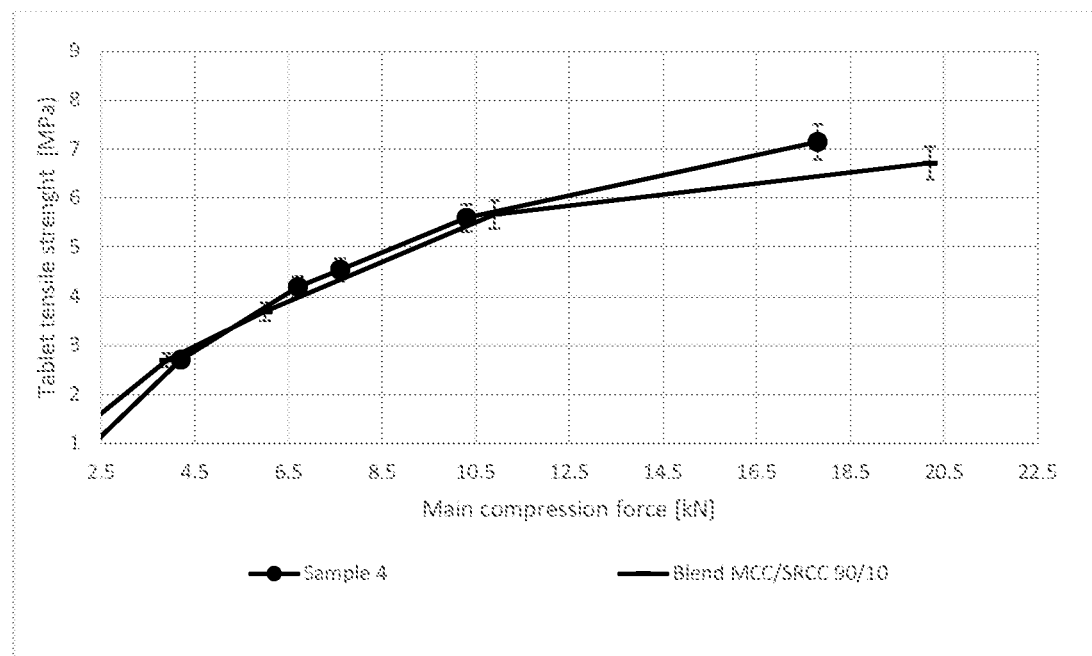
FIG. 4 shows a comparison of the tablet tensile strength [MPa] as a function of the main compression force [kN] for Sample 4 as well as for a simple blend of MCC and SRCC in a proportion of 90:10.

The tablet hardness [N] of the excipients as a function of the main compression force [kN] is shown in FIG. 1. The tablet tensile strength [MPa] of the co-processed compounds as a function of the main compression force [kN] is shown in FIG. 2. FIG. 3 shows a comparison of the tablet hardness [N] as a function of the main compression force [kN] for Sample 4 as well as for a simple blend of MCC and SRCC in a proportion of 90:10. FIG. 4 shows a comparison of the tablet tensile strength [MPa] as a function of the main compression force [kN] for Sample 4 as well as for a simple blend of MCC and SRCC in a proportion of 90:10.

Disintegration Assay

The disintegration test was conducted with a DisiTest 50 Automatic Tablet Disintegration Tester of Pharmatron.

For the testing a beaker was filled with 720 ml distilled water. The water was heated to 37.0° C., and then 6 Tablets were placed in a robust basket.

The apparatus automatically detects and records the disintegration time. In addition, the disintegration time was also monitored visually.

Figure 5:
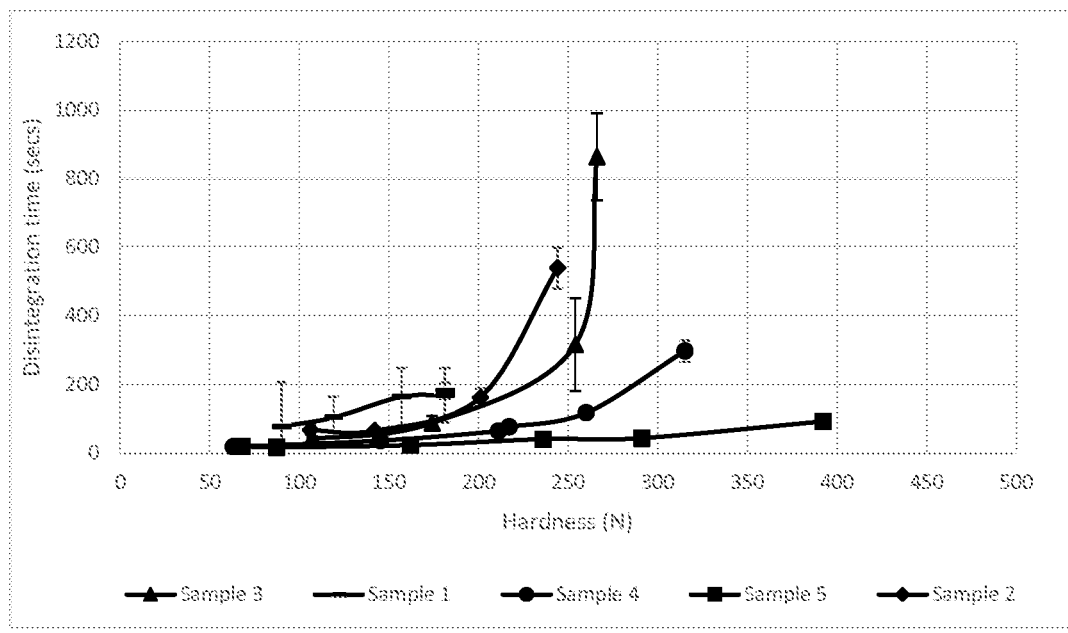
FIG. 5 shows shows the disintegration time [sec] as a function of the tablet hardness [N] for Samples 1 to 4.
Figure 6:
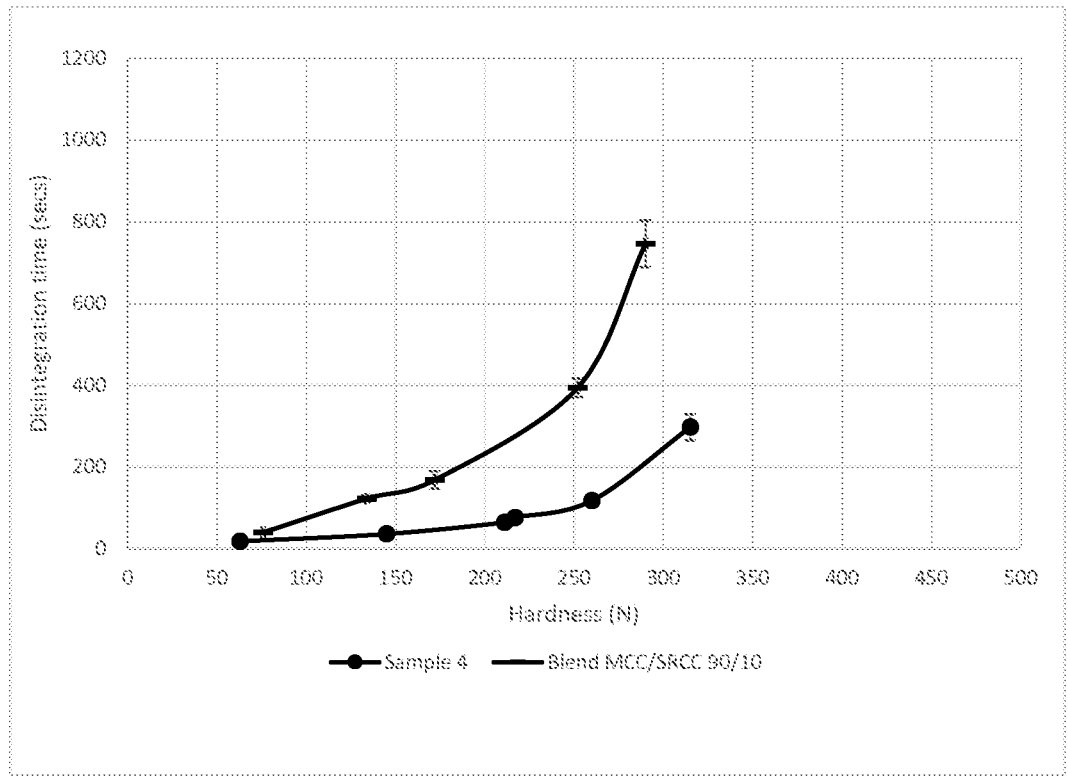
FIG. 6 shows a comparison of the disintegration time [sec] as a function of the tablet hardness [N] for Sample 4 as well as for a simple blend of MCC and SRCC in a proportion of 90:10.

FIG. 5 shows the disintegration time [sec] as a function of the tablet hardness [N] for Samples 1 to 4. FIG. 6 shows a comparison of the disintegration time [sec] as a function of the tablet hardness [N] for Sample 4 as well as for a simple blend of MCC and SRCC in a proportion of 90:10.

Comparison of SRCC vs. GCC

Spray-drying trials for SRCC and GCC were performed on a Niro spray-dryer, Mobile Minor, using a pressure nozzle with the following settings:

Inlet temp: 240° C.
Outlet temp.: 95° C.
Spray pressure: 55%
Pump rpm: 22.3 ml/min
Nozzle orifice: 1 mm Aqueous slurries of mixtures of microcrystalline cellulose (MCC) and surface-reacted calcium carbonate (SRCC) or ground calcium carbonate (GCC) with different proportions were used for the spray drying experiments resulting in the preparation of the excipients. The aqueous slurries featured solids contents of 15 wt.-%, based on the total weight of the slurry.

Tables 3 and 4 show the proportions of microcrystalline cellulose (MCC) to surface-reacted calcium carbonate (SRCC) or ground calcium carbonate (GCC) that have been used to prepare the excipients:

TABLE 3

Proportions of MCC to SRCC

| Sample No. | Microcrystalline cellulose (MCC) (%) | Surface-reacted calcium carbonate (SRCC) (%) |
|---|---|---|
| 1 | 100 | 0 |
| 2 | 98 | 2 |
| 3 | 95 | 5 |
| 4 | 90 | 10 |
| 5 | 75 | 25 |

TABLE 4

Proportions of MCC to GCC

| Sample No. | Microcrystalline cellulose (MCC) (%) | Ground calcium carbonate GCC (%) |
|---|---|---|
| 1 | 100 | 0 |
| 2B | 98 | 2 |
| 3B | 95 | 5 |
| 4B | 90 | 10 |
| 5B | 75 | 25 |

The density and compressibility values of the obtained co-processed excipients set out in Tables 3 and 4 are listed in Tables 5 and 6.

TABLE 5

Density and compressibility values of the co-processed excipients set out in Table 3

| Sample No. | Bulk density [g/ml] | Tapped density [g/ml] | Hausner Ratio | Acc. Ph | Angle of repose [°] | Acc. Ph |
|---|---|---|---|---|---|---|
| 1 | 0.36 | 0.49 | 1.36 | Poor | 46 | Poor |
| 2 | 0.39 | 0.53 | 1.36 | Poor | 42.5 | Passable |
| 3 | 0.41 | 0.52 | 1.27 | Fair | 39.7 | Fair |
| 4 | 0.39 | 0.51 | 1.31 | Passable | 39.0 | Fair |

TABLE 6

Density and compressibility values of the co-processed excipients set out in Table 4

| Sample No. | Bulk density [g/ml] | Tapped density [g/ml] | Hausner Ratio | Acc. Ph | Angle of repose [°] | Acc. Ph |
|---|---|---|---|---|---|---|
| 1 | 0.36 | 0.49 | 1.36 | Poor | 46 | Poor |
| 2B | 0.43 | 0.6 | 1.40 | Poor | 46.2 | Poor |
| 3B | 0.43 | 0.59 | 1.37 | Poor | 43.3 | Passable |
| 4B | 0.45 | 0.64 | 1.42 | Poor | 44.5 | Passable |
| 5B | 0.48 | 0.68 | 1.42 | Poor | 44.8 | Passable |

The obtained excipients set out in Tables 5 and 6 were further mixed with 0.5 wt.-% lubricant (Magnesium stearate, Ligamed MF-2-V, Cas #557-04-0, Peter Greven) in a Turbula Mixer (Willy A. Bachofen, Turbula T10B) for 5 minutes. The mix was further used to prepare tablets in a Fette 1200i using EU1" tooling, a 10 mm fill cam, 8 standard convex round 10 mm punches and a tableting speed of 15000 tablets/hour. The fill depth was adjusted to obtain compression forces of 2 kN up to 20 kN and the tablet weight was fixed at 175 mg.

Figure 7:
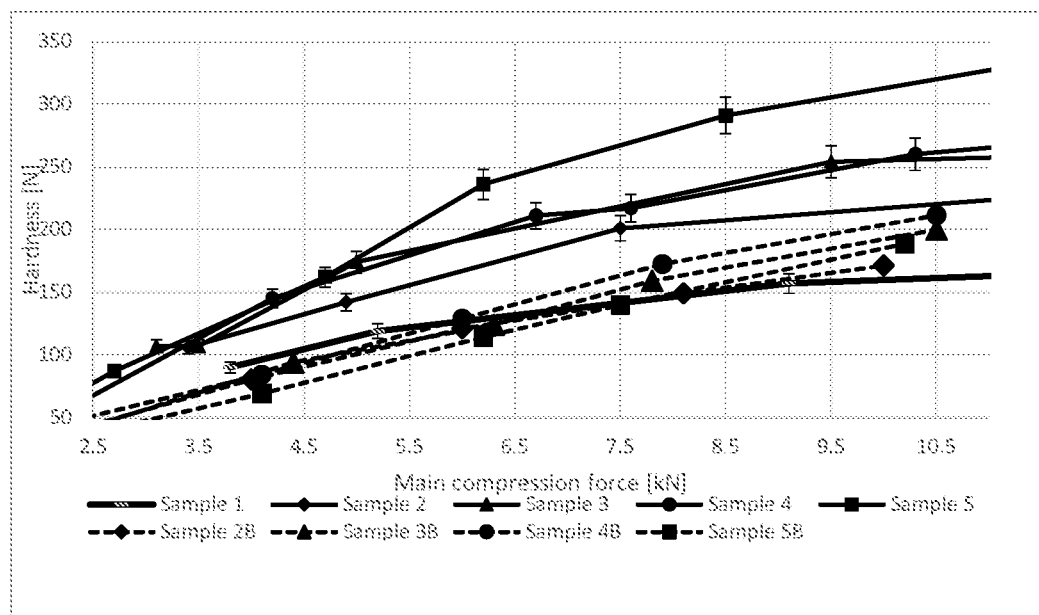
FIG. 7 shows the tablet hardness [N] of the excipients as a function of the main compression force [kN]. Comparison of SRCC (bold) vs GCC (dotted). Sample no. 1 refers to MCC without SRCC or GCC.
Figure 8:
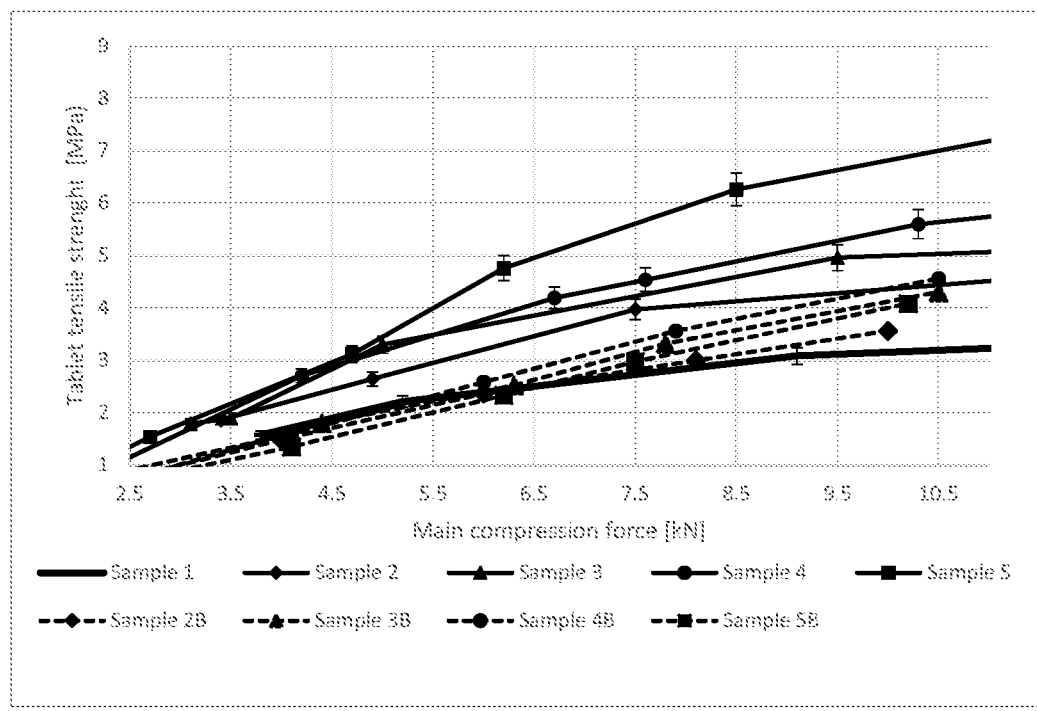
FIG. 8 shows the tablet tensile strength [MPa] of the excipients as a function of the main compression force [kN]. Comparison of SRCC (bold) vs GCC (dotted).

The tablet hardness [N] of the excipients as a function of the main compression force [kN] is shown in FIG. 7. The tablet tensile strength [MPa] of the excipients as a function of the main compression force [kN] is shown in FIG. 8.

The disintegration test was conducted with a DisiTest 50 Automatic Tablet Disintegration Tester of Pharmatron.

For the testing, a beaker was filled with 720 ml distilled water. The water was heated to 37.0° C., and then 6 Tablets were placed in a robust basket.

The apparatus automatically detects and records the disintegration time. In addition, the disintegration time was also monitored visually.

Figure 9:
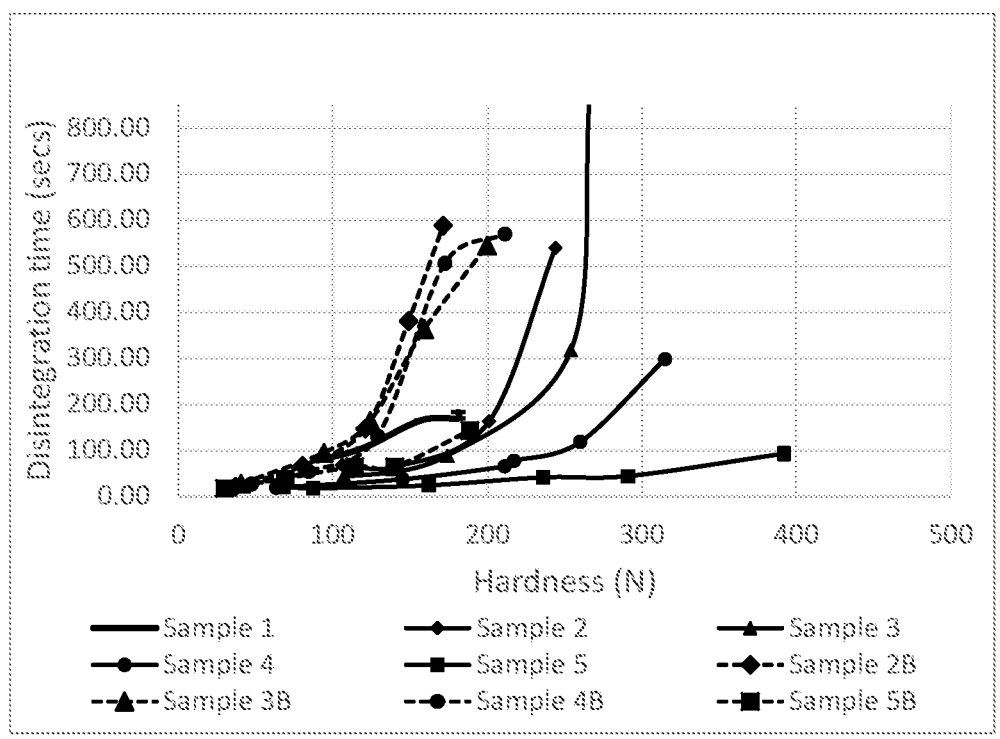
FIG. 9 shows the disintegration time [sec] as a function of the tablet hardness [N]. Comparison of SRCC (bold) vs GCC (dotted). Sample no. 1 refers to MCC without SRCC or GCC.

FIG. 9 shows the disintegration time [sec] as a function of the tablet hardness [N] for the excipients set out Tables 5 and 6.

Comparison of Different Processing Conditions

Trials were performed in which sample no. 3 has been prepared by spray-drying as set out above (see "Comparison of SRCC vs. GCC"). Sample no. 3C has been prepared by dry-co-processing (i.e. in a high-shear mixer) in that a 4 kg blend comprising 5% SRCC and 95% MCC has been produced in a Somakon mixer. The blending was done at a speed of 1000 rpm at ambient temperature for 10 minutes. Sample no. 3D has been prepared by pre-mild milling SRCC followed by dry-co-processing (i.e. in a high-shear mixer) in that the SRCC was ground in the pin mill down to a $d_{50}$ of 4.5 µm and then mixed with MCC in the same way as described for sample no. 3C.

Table 7 shows the proportions of microcrystalline cellulose (MCC) to surface-reacted calcium carbonate (SRCC) that have been used to prepare the excipients:

TABLE 7

Proportions of MCC to SRCC

| Sample No. | Microcrystalline cellulose (MCC) (%) | Surface-reacted calcium carbonate (SRCC) (%) |
|---|---|---|
| 3 | 95 | 5 |
| 3C | 95 | 5 |
| 3D | 95 | 5 |

The density and compressibility values of the obtained co-processed excipients set out in Table 7 are listed in Table 8.

TABLE 8

Density and compressibility values of the co-processed excipients set out in Table 7

| Sample No. | Bulk density [g/ml] | Tapped density [g/ml] | Hausner Ratio | Acc. Ph | Angle of repose [°] | Acc. Ph |
|---|---|---|---|---|---|---|
| 3 | 0.41 | 0.52 | 1.27 | Fair | 39.7 | Fair |
| 3C | 0.47 | 0.64 | 1.36 | Poor | 43 | Passable |
| 3D | 0.48 | 0.65 | 1.36 | Poor | 43 | Passable |

Figure 10:
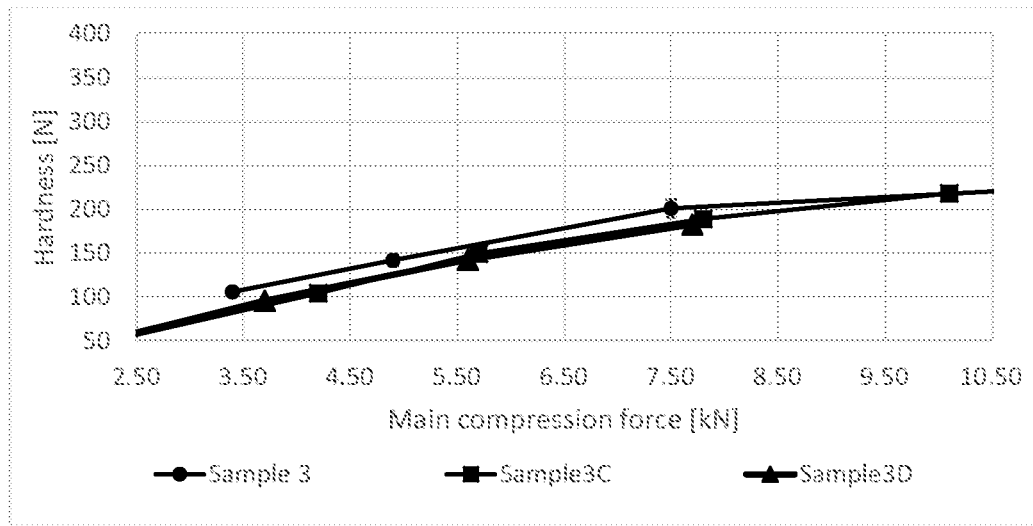
FIG. 10 shows the tablet hardness [N] of the excipients as a function of the main compression force [kN].
Figure 11:
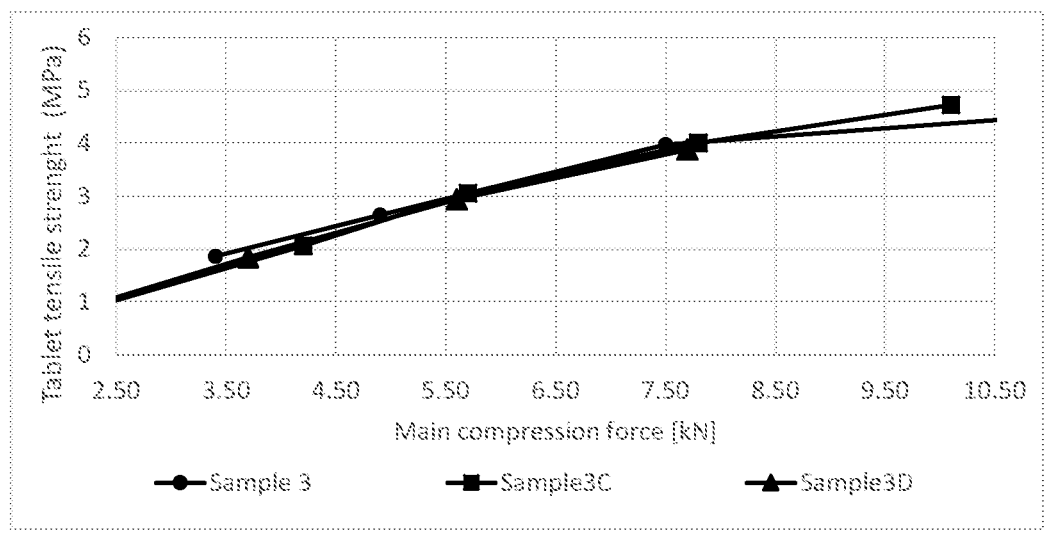
FIG. 11 shows the tablet tensile strength [MPa] of the excipients as a function of the main compression force [kN].

FIG. 10 shows a comparison of the tablet hardness [N] of the excipients as a function of the main compression force [kN]. FIG. 11 shows a comparison of the tablet tensile strength [MPa] of the excipients as a function of the main compression force [kN].

The disintegration test was conducted with a DisiTest 50 Automatic Tablet Disintegration Tester of Pharmatron.

For the testing, a beaker was filled with 720 ml distilled water. The water was heated to 37.0° C., and then 6 Tablets were placed in a robust basket.

The apparatus automatically detects and records the disintegration time. In addition, the disintegration time was also monitored visually.

Figure 12:
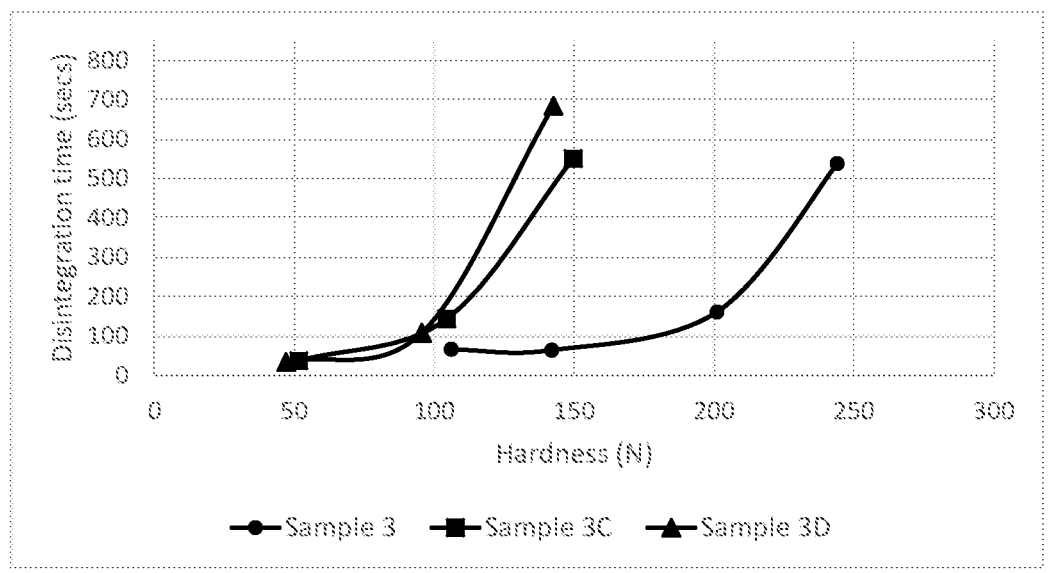
FIG. 12 shows the disintegration time [sec] as a function of the tablet hardness [N].

FIG. 12 shows the disintegration time [sec] as a function of the tablet hardness [N] for the samples set out Table 8.

The invention claimed is:

1. Particulate pharmaceutical or nutraceutical excipient comprising
    a) microcrystalline cellulose, and
    b) surface-reacted calcium carbonate, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source,
    wherein the weight ratio of the microcrystalline cellulose to the surface-reacted calcium carbonate is from 99:1 to 80:20.

2. The particulate pharmaceutical or nutraceutical excipient according to claim 1, wherein the surface-reacted calcium carbonate has
    i) a volume median particle size $d_{50}$ from 0.5 to 50 µm, and/or
    ii) a BET specific surface area of from 5 to 200 m²/g, measured using nitrogen and the BET method according to ISO 9277:2010, and/or
    iii) an intra-particle intruded specific pore volume in the range from 0.1 to 2.3 cm³/g, calculated from mercury porosimetry measurement.

3. The particulate pharmaceutical or nutraceutical excipient according to claim 1, wherein
    i) the natural ground calcium carbonate is selected from the group consisting of marble, chalk, limestone, and mixtures thereof, or
    ii) the precipitated calcium carbonate is selected from the group consisting of precipitated calcium carbonates having an aragonitic, vateritic or calcitic crystal form, and mixtures thereof.

4. The particulate pharmaceutical or nutraceutical excipient according to claim 1, wherein the at least one $H_3O^+$ ion donor is selected from the group consisting of hydrochloric acid, sulphuric acid, sulphurous acid, phosphoric acid, citric acid, oxalic acid, an acidic salt, acetic acid, formic acid, and mixtures thereof.

5. The particulate pharmaceutical or nutraceutical excipient according to claim 1, wherein the microcrystalline cellulose has a
    i) a loose bulk density from 0.20 to 0.52 g/ml, and/or
    ii) a weight median particle size $d_{50}$ from 10 to 1000 µm.

6. The particulate pharmaceutical or nutraceutical excipient according to claim 1, wherein the weight ratio of the microcrystalline cellulose to the surface-reacted calcium carbonate is from 98:2 to 90:10.

7. The particulate pharmaceutical or nutraceutical excipient according to claim 1, wherein the excipient comprises co-processed microcrystalline cellulose and surface-reacted calcium carbonate in that the surface-reacted calcium carbonate is in intimate association with the microcrystalline cellulose.

8. The particulate pharmaceutical or nutraceutical excipient according to claim 1, wherein the excipient has a loose bulk density from 0.25 to 0.90 g/ml.

9. The particulate pharmaceutical or nutraceutical excipient according to claim 2, wherein the surface-reacted calcium carbonate has i) a volume median particle size $d_{50}$ from 1.5 to 15 µm, and/or ii) a BET specific surface area of from 40 to 100 m²/g, measured using nitrogen and the BET method according to ISO 9277:2010, and/or iii) an intra-particle intruded specific pore volume in the range from 0.6 to 1.6 cm³/g, calculated from mercury porosimetry measurement.

10. The particulate pharmaceutical or nutraceutical excipient according to claim 4, wherein the at least one $H_3O^+$ ion donor is phosphoric acid.

11. The particulate pharmaceutical or nutraceutical excipient according to claim 5, wherein the microcrystalline cellulose has a
i) a loose bulk density from 0.26 to 0.36 g/ml, and/or
ii) a weight median particle size $d_{50}$ from 20 to 200 µm.

12. The particulate pharmaceutical or nutraceutical excipient according to claim 8, wherein the excipient has a loose bulk density from 0.25 to 0.65 g/ml.

13. A pharmaceutical or nutraceutical composition comprising the particulate pharmaceutical or nutraceutical excipient according to claim 1 and optionally at least one active ingredient.

14. The pharmaceutical or nutraceutical composition according to claim 13, wherein the pharmaceutical or nutraceutical composition further comprises at least one adjuvant selected from the group comprising natural or synthetic scenting agents, natural or synthetic flavoring agents, natural or synthetic coloring agents, natural or synthetic sweeteners, lubricants, disintegrants, glidants, and mixtures thereof.

15. A pharmaceutical or nutraceutical composition comprising the particulate pharmaceutical or nutraceutical excipient according to claim 13, wherein the at least one active ingredient is selected from the group consisting of pharmaceutically or nutraceutically active ingredients, inactive pharmaceutical or nutraceutical precursors, biologically active ingredients, inactive biological precursors and mixtures thereof.

16. A process for the preparation of the particulate pharmaceutical or nutraceutical excipient according to claim 1, the process comprising the steps of:
a) mixing microcrystalline cellulose and surface-reacted calcium carbonate, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source, in a weight ratio of the microcrystalline cellulose to the surface-reacted calcium carbonate from 99:1 to 80:20, and
b) co-processing the mixture obtained in step a) obtaining thereby the particulate pharmaceutical or nutraceutical excipient.

17. The process according to claim 16, wherein co-processing step b) is performed by dry- or wet-processing.

18. The process according to claim 16, wherein mixing step a) is performed in an aqueous medium such as to form an aqueous slurry comprising the microcrystalline cellulose and the surface-reacted calcium carbonate.

19. A process for manufacturing a pharmaceutical or nutraceutical composition according to claim 13, the process comprises the steps of:
i) providing a particulate pharmaceutical or nutraceutical excipient according to claim 1,
ii) subjecting the particulate pharmaceutical or nutraceutical excipient to dry granulation, wet granulation, melt granulation or direct compression.

20. The process according to claim 19, further comprising a step c) of contacting the particulate pharmaceutical or nutraceutical excipient before step b) or the composition obtained in step b) with at least one active ingredient, and/or at least one adjuvant selected from the group comprising natural or synthetic scenting agents, natural or synthetic flavoring agents, natural or synthetic coloring agents, natural or synthetic sweeteners, lubricants, disintegrants, glidants, and mixtures thereof.

* * * * *